United States Patent
Goddard et al.

(10) Patent No.: US 6,534,061 B1
(45) Date of Patent: Mar. 18, 2003

(54) TUMOR NECROSIS FACTOR RECEPTOR HOMOLOGS AND NUCLEIC ACIDS ENCODING THE SAME

(75) Inventors: Audrey Goddard, San Francisco; James Pan, Belmont; Minhong Yan, Burlingame, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/548,130

(22) Filed: Apr. 12, 2000

Related U.S. Application Data
(60) Provisional application No. 60/128,849, filed on Apr. 12, 1999.

(51) Int. Cl.[7] .............................................. A61K 39/00
(52) U.S. Cl. ................. 424/192.1; 530/350; 530/387.3; 530/402; 530/413; 536/23.4; 536/23.5; 424/178.1; 424/185.1; 514/2
(58) Field of Search .............................. 530/387.3, 350, 530/402, 413; 536/23.5, 23.4; 424/185.1, 178.1, 192.1; 435/69.7, 69.8

(56) References Cited

FOREIGN PATENT DOCUMENTS

| EP | 307247 | 3/1989 |
|----|--------|--------|
| EP | 417563 | 3/1991 |
| WO | WO 97/01633 | 1/1997 |
| WO | WO 97/25428 | 7/1997 |
| WO | WO 98/18921 | 5/1998 |
| WO | WO 98/24826 | 7/1998 |
| WO | WO 99/19490 | 4/1999 |
| WO | WO 00/01817 | 1/2000 |

OTHER PUBLICATIONS

Yan et al., "Two–Amino Acid Molecular Switch in an Epithelial Morphogen That Regulates Binding to Two Distinct Receptors" *Science* 290:523–527 (2000).
Amakawa et al., "The Hodgkin Disease Antigen CD30 is Crucial for Antigen–induced Death of Developing T Cells" *Cold Spring Harbor Laboratory Symposium on Programmed Cell Death* (Abstr. No. 10) (1995).
Armitage et al., "Molecular and biological characterization of a murine ligand for CD40" *Nature* 357(6373):80–82 (May 7, 1992).
Ashkenazi and Dixit, "Death receptors: signaling and modulation" *Science* 281(5381):1305–1308 (Aug. 28, 1998).
Ashkenazi et al., "Protection Against Endotoxic Shock by a Tumor Necrosis Factor Receptor Immunoadhesin" *Proc. Natl. Acad. Sci.* 88:10535–10539 (Dec. 1991).
Baldwin, "The NF–κB and IκB Proteins: New Discoveries and Insights" *Ann. Rev. Immunol.* 14:649–683 (1996).
Banner et al., "Crystal Structure of the Soluble Human 55 kd TNF Receptor–Human TNFβ Complex: Implications for TNF Receptor Activation" *Cell* 73:431–445 (1993).

Barr et al., "Apoptosis and Its Role in Human Disease" *Bio/Technology* 12:487–493 (1994).
Bayes et al., "The anhidrotic ectodermal dysplasia gene (EDA) undergoes alternative splicing and encodes ectodysplasin–A with deletion mutations in collagenous repeats" *Human Molecular Genetics* 7(11):1661–1669 (Oct. 1998).
Bodmer et al., "TRAMP, a Novel Apoptosis–Mediating Receptor with Sequence Homology to Tumor Necrosis Factor Receptor 1 and Fas(Apo–1/CD95)" *Immunity* 6:79–88 (1997).
Boldin et al., "Involvement of MACH, a Novel MORT1/FADD–Interacting Protease, in Fas/APO–1–and TNF Receptor–Induced Cell Death" *Cell* 85:803–815 (1996).
Boldin et al., "Self–Association of the "Death Domains" of the p55 Tumor Necrosis Factor (TNF) Receptor and Fas/APO1 Prompts Signaling for TNF and Fas/APO1 Effects" *Journal of Biological Chemistry* 270:387–391 (1995).
Bolivar et al., "Construction and Characterization of New Cloning Vehicles. II. A Multipurpose Cloning System" *Gene* 2:95–113 (1977).
Brockhaus et al., "Identification of two types of tumor necrosis factor receptors on human cell lines by monoclonal antibodies" *Proc. Natl. Acad. Sci. USA* 87:3127–3131 (1990).
Brojatsch et al., "CAR1, a TNFR–Related Protein, Is a Cellular Receptor for Cytopathic Avian Leukosis–Sarcoma Viruses and Mediates Apoptosis" *Cell* 87:845–855 (Nov. 29, 1996).
Browning et al., "Lymphotoxin β, a Novel Member of the TNF Family That Forms a Heteromeric Complex with Lymphotoxin on the Cell Surface" *Cell* 72:847–856 (1993).
Cao et al., "IRAK: a kinase associated with the interleukin–1 receptor" *Science* 271(5252):1128–1131 (Feb. 23, 1996).
Chicheportiche et al., "TWEAK, a new secreted ligand in the tumor necrosis factor family that weakly induces apoptosis" *Journal of Biological Chemistry* 272(51):32401–32410 (Dec. 19, 1997).
Chinnaiyan and Dixit, "The Cell–Death Machine" *Current Biology* 6:555–562 (1996).

(List continued on next page.)

Primary Examiner—Lorraine Spector
Assistant Examiner—Eileen B. O'Hara
(74) Attorney, Agent, or Firm—Diane L. Marschang

(57) ABSTRACT

The present invention is directed to novel polypeptides having homology to members of the tumor necrosis factor receptor family and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

32 Claims, 12 Drawing Sheets

(3 of 12 Drawing Sheet(s) Filed in Color)

OTHER PUBLICATIONS

Chinnaiyan et al., "FADD, a novel death domain–containing protein, interacts with the death domain of Fas and initiates apoptosis" *Cell* 81:505–512 (1995).

Chinnaiyan et al., "FADD/MORT1 Is a Common Mediator of CD95 (Fas/APO–1) and Tumor Necrosis Factor Receptor–induced Apoptosis" *Journal of Biological Chemistry* 271:4961–4965 (1996).

Chinnaiyan et al., "Interaction of CED–4 with CED–3 and CED–9: A Molecular Framework for Cell Death" *Science* 275:1122–1126 (1997).

Chinnaiyan et al., "Signal Transduction by DR3, a Death Domain–Containing Receptor Related to TNFR–1 and CD95" *Science* 274:990–992 (1996).

Cleveland and Ihle, "Contenders in FasL/TNF Death Signaling" *Cell* 81:479–482 (1995).

Dealtry et al., "DNA Fragmentation and Cytotoxicity Caused by Tumor Necrosis Factor is Enhanced by Interferon–$\gamma$" *European Journal of Immunology* 17:689–693 (1987).

Degli–Esposti et al., "Cloning and Characterization of TRAIL–R3, a Novel Member of the Emerging TRAIL Receptor Family" *Journal of Experimental Medicine* 186(7):1165–1170 (Oct. 6, 1997).

Degli–Esposti et al., "The Novel Receptor TRAIL–R4 Induces NF–$\kappa$B and Protects against TRAIL–Mediated Apoptosis, yet Retains an Incomplete Death Domain" *Immunity* 7:813–820 (1997).

Enari et al., "Involvement of an ICE–like protease in Fas–mediated Apoptosis" *Nature* 375:78–81 (1995).

Fraser and Evan, "A License to Kill" *Cell* 85:781–784 (1996).

Golstein, "Cell Death: TRAIL and Its Receptors" *Curr. Biol* 7:R750–R753 (1997).

Goodwin et al., "Molecular and biological characterization of a ligand for CD27 defines a new family of cytokines with homology to tumor necrosis factor" *Cell* 73(3):447–456 (May 7, 1993).

Goodwin et al., "Molecular cloning and expression of the type 1 and type 2 murine receptors for tumor necrosis factor" *Molecular & Cellular Biology* 11:3020–3026 (1991).

Goodwin et al., "Molecular cloning of a ligand for the inducible T cell gene 4–IBB: a member of an emerging family of cytokines with homology to tumor necrosis factor" *European Journal of Immunology* 23(10):2631–2641 (Oct. 1993).

Gruss and Dower, "Tumor Necrosis Factor Ligand Superfamily: Involvement in the Pathology of Malignant Lymphomas" *Blood* 85:3378–3404 (1995).

Gurney et al., "Identification of a new member of the tumor necrosis factor family and its receptor, a human ortholog of mouse GITR" *Current Biology* 9(4):215–218 (Feb. 25, 1999).

Hahne et al., "APRIL, a new ligand of the tumor necrosis factor family, stimulates tumor cell growth" *Journal of Experimental Medicine* 188(6):1185–1190 (Sep. 21, 1998).

Hale et al., "Demonstration of in vitro and in vivo efficacy of two biologically active human soluble TNF receptors expressed in *E. coli*" *J. Cell Biochem.* (abstract only Supplement 15F; P 424) pps. 113 (1991).

Harbury et al., "A switch between two–, three–. and four–standard coiled coils in GCN4 leucine zipper mutants" *Science* 262(5138):1401–1407 (Nov. 26, 1993).

Hohmann et al., "Two different cell types have different major receptors for human tumor necrosis factor (TNF$\alpha$)" *Journal of Biological Chemistry* 264(25):14927–14934 (1989).

Holmes et al., "Structure and Functional Expression of a Human Interleukin–8 Receptor" *Science* 253(5025):1278–1280 (Sep. 13, 1991).

Hsu et al., "TRADD–TRAF2 and TRADD–FADD interactions define two distinct TNF receptor 1 signal transduction pathways" *Cell* 84:299–308 (1996).

Hu et al., "Characterization of TNFRSF19, a novel member of the tumor necrosis factor receptor superfamily" *Genomics* 62(1):103–107 (Nov. 15, 1999).

Itoh et al., "The polypeptide encoded by the cDNA for human cell surface antigen Fas can mediate apoptosis" *Cell* 66:233–243 (1991).

Johnson et al., "Expression and Structure of the Human NGF Receptor" *Cell* 47:545–554 (Nov. 21, 1986).

Kere et al., "X–linked anhidrotic (hypohidrotic) ectodermal dysplasia is caused by mutation in a novel transmembrane protein" *Nature Genetics* 13(4):409–416 (Aug. 1996).

Kitson et al., "A Death–Domain–Containing Receptor that Mediates Apoptosis" *Nature* 384:372–375 (1996).

Kohno et al., "A second tumor necrosis factor receptor gene product can shed a naturally occurring tumor necrosis factor inhibitor" *Proc. Natl. Acad. Sci. USA* 87:8331–8335 (1990).

Krammer et al., "Regulation of Apoptosis in the Immune System" *Curr. Op. Immunol.* 6:279–289 (1994).

Lewis et al., "Cloning and expression of cDNAs for two distinct murine tumor necrosis factor receptors demonstrate one receptor is species specific" *Proc. Natl. Acad. Sci. USA* 88:2830–2834 (1991).

Loetscher et al., "Molecular Cloning and Expression of the Human 55 kd Tumor Necrosis Factor Receptor" *Cell* 61:351–359 (Apr. 20, 1990).

MacFarlane et al., "Identification and Molecular Cloning of Two Novel Receptors for the Cytotoxic Ligand TRAIL" *Journal of Biological Chemistry* 272(41):25417–25420 (Oct. 10, 1997).

Malinin et al., "MAP3K–related Kinase involved in NF–$\kappa$B induction by TNF, CD95 and IL–1" *Nature* 385(6616):540–544 (Feb. 6, 1997).

Mallett et al., "Characterization of the MRC OX40 Antigen of Activated CD4 Positive T Lymphocytes—A Molecule Related to Nerve Growth Factor Receptor" *EMBO Journal* 9(4):1063–1068 (Apr. 1990).

Marsters et al., "A Novel Receptor for Apo2L/TRAIL Contains a Truncated Death Domain" *Current Biology* 7:1003–1006 (1997).

Marsters et al., "Activation of Apoptosis by Apo–2 Ligand is Independent of FADD but Blocked by CrmA" *Current Biology* 6(6):750–752 (1996).

Marsters et al., "Apo–3 a New Member of the Tumor Necrosis Factor Receptor Family, Contains a Death Domain and Activates Apoptosis and $\kappa$B" *Curr. Biol.* 6(12):1669–1676 (1996).

Marsters et al., "Herpesvirus Entry Mediator, A Member of the Tumor Necrosis Factor (TNFR) Family, Interacts with Members of the TNFR–associated Factor Family and Activates the Transcription Factors NF–$\kappa$B and AP–1" *Journal of Biological Chemistry* 272 (22):14029–14032 (1997).

Marsters et al., "Identification of a ligand for the death–domain–containing receptor Apo3" *Current Biology* 8(9):525–528 (Apr. 23, 1998).

Mongkolsapaya et al., "Cutting Edge: Lymphocyte inhibitor of TRAIL (TNF–related apoptosis–inducing ligand): a new receptor protecting lymphocytes from the death ligand TRAIL" *Journal of Immunology* 160(1):3–6 (Jan. 1, 1998).
Montgomery et al., "Herpes Simplex Virus–1 Entry into Cells Mediated by a Novel Member of the TNF/NGF Receptor Family" *Cell* 87(3):427–436 (1996).
Moore et al., "BLyS: member of the tumor necrosis factor family and B lymphyocyte stimulator" *Science* 285(5425):260–263 (Jul. 9, 1999).
Muzio et al., "FLICE, A Novel FADD–Homologous ICE/CED–3–like Protease, Is Recruited to the CD95 (Fas/APO–1) Death–Inducing Signaling Complex" *Cell* 85:817–827 (1996).
Muzio et al., "IRAK (Pelle) family member IRAK–2 and MyD88 as proximal mediators of IL–1 signaling" *Science* 278(5343):1612–1615 (Nov. 28, 1997).
Nagata et al., "The Fas Death Factor" *Science* 267:1449–1456 (1995).
Nagata, "Apoptosis by Death Factor" *Cell* 88:355–365 (1997).
Naismith and Sprang, "Modularity in the TNF–receptor family" *Trends in Biochemical Sciences* 23:74–79 (Feb. 1998).
Nocentini et al., "A new member of the tumor necrosis factor/nerve growth factor receptor family inhibits T cell receptor–induced apoptosis" *Proc. Natl. Acad. Sci.* 94(12):6216–6221 (Jun. 10, 1997).
Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor" *EMBO Journal* 9:3269–3278 (1990).
Pan et al., "An Antagonist Decoy Receptor and a Death–domain Containing Receptor for TRAIL" *Science* 277:815–818 (1997).
Pan et al., "Identification and functional characterization of DR6, a novel death domain–containing TNF receptor" *FEBS Letters* 431(3):351–356 (Jul. 24, 1998).
Pan et al., "The Receptor for the Cytotoxic Ligand TRAIL" *Science* 276:111–113 (1997).
Pan et al., "TRUNDD, a new member of the TRAIL receptor family that antagonizes TRAIL signalling" *FEBS Letters* 424(1–2):41–45 (Mar. 6, 1998).
Peetre et al., "A tumor necrosis factor binding protein is present in human biological fluids" *European Journal of Haematology* 41:414–419 (1988).
Pennica et al., "Human Tumour Necrosis Factor: Precursor Structure, Expression and Homology to Lymphotoxin" *Nature* 312;724–729 (1984).
Pitti et al., "Genomic amplification of a decoy receptor for Fas ligand in lung and colon cancer" *Nature* 396(6712):699–703 (Dec. 17, 1998).
Pitti et al., "Induction of Apoptosis by Apo–2 Ligand, a New Member of the Tumor Necrosis Factor Cytokine Family" *Journal of Biological Chemistry* 271:12687–12690 (1996).
Radeke et al., "Gene transfer and molecular cloning of the rat nerve growth factor receptor" *Nature* 325:593–597 (Feb. 12, 1987).
Raff, "Social Controls on Cell Survival and Cell Death" *Nature* 356:397–400 (1992).
Ray et al., "Viral Inhibition of Inflammation: Cowpox Virus Encodes an Inhibitor of the Interleukin–1β Converting Enzyme" *Cell* 69:597–604 (May 15, 1992).

Rothe et al., "A novel family of putative signal transducers associated with the cytoplasmic domain of the 75 kDA tumor necrosis factor receptor" *Cell* 78:681–682 (1994).
Rothe et al., "TRAF2–mediated activation of NF–κB by TNF receptor 2 and CD40" *Science* 269(5229):1424–1427 (Sep. 8, 1995).
Ruppert et al., "Cloning and Expression of Human $TAF_{II}250$: a TBP–associated Factor Implicated in Cell–cycle Regulation" *Nature* 362:175–179 (1993).
Sachs et al., "Control of Programmed Cell Death in Normal and Leukemic Cells: New Implications for Therapy" *Blood* 82:15–21 (1993).
Schall et al., "Molecular Cloning and Expression of a Receptor for Human Tumor Necrosis Factor" *Cell* 61;361–370 (Apr. 20, 1990).
Schmid et al., "DNA Fragmentation: Manifestation of Target Cell Destruction Mediated by Cytotoxic T–cell Lines, Lymphotoxin–secreting Helper T–cell Clones, and Cell–free Lymphotoxin–containing Supernatant" *Proc. Natl. Acad. Sci. USA* 83:1881–1885 (1986).
Schneider et al., "Characterization of two receptors for TRAIL" *FEBS Letters* 416:329–334 (1997).
Screaton et al., "LARD: A new lymphoid–specific death domain containing receptor regulated by alternative pre–mRNA splicing" *Proc. Natl. Acad. Sci.* 94:4615–4619 (1997).
Screaton et al., "TRICK2, a new alternatively spliced receptor that transduces the cytotoxic signal from TRAIL" *Current Biology* 7:693–696 (1997).
Seckinger et al., "Purification and biologic characterization of a specific tumor necrosis factor α Inhibitor" *Journal of Biological Chemistry* 264:11966–11973 (1989).
Sheridan et al., "Control of TRAIL–induced Apoptosis by a Family of Signaling and Decoy Receptors" *Science* 277:818–821 (1997).
Simonet et al. "Osteoprotegerin: A Novel Secreted Protein Involved in the Regulation of Bone Density" *Cell* 89:309–319 (Apr. 18, 1997).
Smith et al., "A Receptor for Tumor Necrosis Factor Defines an Unusual Family of Cellular and Viral Proteins" *Science* 248:1019–1023 (May 25, 1990).
Smith et al., "CD30 antigen, a marker for Hodgkin's lymphoma, is a receptor whose ligand defines an emerging family of cytokines with homology to TNF" *Cell* 73(7):1349–1360 (Jul. 2, 1993).
Smith et al., "T2 Open reading frame from the shope fibroma virus encodes a soluble form of the TNF receptor" *Biochem. & Biophys. Res. Comm.* 176:335–342 (1991).
Sompayrac et al., "Efficient infection of monkey cells with DNA of simian virus 40" *Proc. Natl. Acad. Sci. USA* 78(12):7575–7578 (Dec. 1981).
Stamenkovic et al., "A B–lymphocyte activation molecular related to the nerve growth factor receptor and induced by cytokines in carcinomas" *EMBO Journal* 8(5):1403–1410 (1989).
Steller et al., "Mechanisms and genes of cellular suicide" *Science* 257:1445–1449 (Mar. 11, 1995).
Takao et al., "Novel DNA Polymorphism in the Mouse Tumor Necrosis Factor Receptors Type 1 and Type 2" *Immunogenetics* 37:199–203 (1993).
Tartaglia et al., "A novel domain within the 55 kd TNF receptor signals cell death" *Cell* 74(5):845–853 (1993).
Tartaglia et al., "Identification and expression cloning of a leptin receptor, ob–r" *Cell* 83:1263–1271 (1995).

Tewari et al., "Fas–and Tumor Necrosis Factor–induced Apoptosis Is Inhibited by the Poxvirus crmA Gene Product" *Journal of Biological Chemistry* 270:3255–3260 (1995).

Tewari et al., "Recent Advances in Tumor Necrosis Factor and CD40 Signaling" *Curr. Op. Genet. Develop.* 6:39–44 (1996).

Tewari et al., "Yama/CPP32β, a Mammalian Homolog of CED–3, Is a CrmA–Inhibitable Protease That Cleaves the Death Substrate Poly(ADP–Ribose) Polymerase" *Cell* 81:801–809 (1995).

Thimmappaya et al., "Adenovirus VAI RNA is required for efficient translation of viral mRNAs at late times after infection" *Cell* 31(3 Pt 2):543–551 (Dec. 1982).

Thompson, "Apoptosis in the Pathogenesis and Treatment of Disease" *Science* 267:1456–1462 (1995).

Ting et al., "RIP mediates tumor necrosis factor receptor 1 activation of NF–κB but not Fas/APO–1–initiated apoptosis" *EMBO Journal* 15(22):6189–6196 (Nov. 15, 1996).

Upton et al., "Myxoma virus expresses a secreted protein with homology to the tumor necrosis factor receptor gene family that contributes to viral virulence" *Virology* 184:370–382 (1991).

Upton et al., "Tumorigenic poxviruses: genomic organization and DNA sequence of the telomeric region of the shope fibroma virus genome" *Virology* 160:20–30 (1987).

Verma et al., "Rel/NF–κB/IκB Family: Intimate Tales of Association and Dissociation" *Genes Develop.* 9:2723–2735 (1995).

Walczak et al., "TRAIL–R2: a novel apoptosis–mediating receptor for TRAIL" *EMBO Journal* 16(17):5386–5397 (1997).

Watanabe–Fukunaga et al., "Lymphoproliferation Disorder in Mice Explained by Defects in Fas Antigen that Mediates Apoptosis" *Nature* 356:314–317 (1992).

Welcher et al., "Nerve growth factor binding of the nerve growth factor receptor" *Proc. Natl. Acad. Sci. USA* 88:159–163 (1991).

Wesche et al., "MyD88: an adapter that recruits IRAK to the IL–1 receptor complex" *Immunity* 7(6):837–847 (Dec. 1997).

Wiley et al., "Identification and Characterization of a New Member of the TNF Family that Induces Apoptosis" *Immunity* 3:673–682 (1995).

Wu et al., "KILLER/DR5 is a DNA damage–inducible p53–regulated death receptor gene" *Nature Genetics* 17:141–143 (Oct. 1997).

Yan and Chao, "Disruption of Cysteine–rich repeats of the p75 nerve growth factor receptor leads to loss of ligand binding" *Journal of Biological Chemistry* 266:12099–12104 (1991).

Yang et al., "Toll–like receptor–2 mediates lipopolysaccharide–induced cellular signalling" *Nature* 395(6699):284–288 (Sep. 17, 1998).

Yonehara et al., "A cell–killing monoclonal antibody (anti––Fas) to a cell surface antigen co–downregulated with the receptor of tumor necrosis factor" *Journal of Experimental Medicine* 169:1747–1756 (1989).

Zheng et al., "Induction of Apoptosis in Mature T Cells by Tumor Necrosis Factor" *Nature* 377:348–351 (1995).

Zou et al., "Apaf–1, a Human Protein Homologous to C. elegans CED–4, Participates in Cytochrome c–Dependent Activation of Caspase–3" *Cell* 90:405–413 (1997).

```
  1 ACCATGGATT GCCAAGAAAA TGAGTACTGG GACCAATGGG GACGGTGTGT CACCTGCCAA CGGTGTGGTC CTGGACAGGA GCTATCCAAG GATTGTGGTT
    TGGTACCCTAA CGGTTCTTTT ACTCATGACC CTGGTTACCC CTGCCACACA GTGGACGGTT GCCACACCAG GACCCTGTCCT CGATAGGTTC CTAACACCAA
                 ^ORF starts here
                              ^cysteine-rich repeat 1

101 ATGGAGAGGG TGGAGATGCC TACTGCACAG CCTGCCCTCC AAAAGCAGCT GGGGCCACCA CAGATGTCAG AGTTGCATCA CCTGTGCTGT
    TACCTCTCCC ACCTCTACGG ATGACGTGTC GGACGGGAGG AGCGTCCATG TTTTCGTCGA CCCCGGTGGT GTCTACAGTC TCAACGTAGT GGACACGACA
                                                           ^cysteine-rich repeat 2

201 CATCAATCGT GTTCAGAAGG TCAACTGCAC AGCTACCTCT AATGCTGTCT GTGGGGACTG TTTGCCCAGG TTCTACCGAA AGACACGCAT TGGAGGCCTG
    GTAGTTAGCA CAAGTCTTCC AGTTGACGTG TCGATGGAGA TTACGACAGA CACCCCTGAC AAACGGGTCC AAGATGGCTT TCTGTGCGTA ACCTCCGGAC
                                                                      ^cysteine-rich repeat 3

301 CAGGACCAAG AGTGCATCCC GTGCACGAAG CAGACCCCCA CCTCTGAGGT TTCCAGTTGA GCTTAGTGGA GGCAGATGCA CCCACAGTGC
    GTCCTGGTTC TCACGTAGGG CACGTGCTTC GTCTGGGGGT GGAGACTCCA AGGTCAACT CGAATCACCT CCGTCTACGT GGGTGTCACG

401 CCCCTCAGGA GGCCACACTT GTTGCACTGG TGAGCAGCCT GCTAGTGGTG TTTACCCTGG GCTCTTCTTC CTCTACTGCA AGCAGTTCTT
    GGGGAGTCCT CCGGTGTGAA CAACGTGACC ACTCGTCGGA CGATCACCAC AAATGGGACC CGAGAAGAAG GAGATGACGT TCGTCAAGAA
                                  ^transmembrane domain 501 CAACAGACAT TGCCAGCGTG TTACAGGAGG TTTGCTGCAG TTTGAGGCTG ATAAAACAGC AAAGGAGGAA TCTCTCTTCC CCGTGCCACC CAGCAAGGAG
    GTTGTCTGTA ACGGTCGCAC AATGTCCTCC AAACGACGTC AAACTCCGAC TATTTTGTCG TTTCCTCCTT AGAGAGAAGG GGCACGGTGG GTCGTTCCTC 601 ACCAGTGCTG AGTCCAAGT GAGTGAGAAC ATCTTTCAGA CCCAGCCACT TAACCCTATC CTCGAGGACG ACTGCAGCTC GACTAGTGGC TTCCCCACAC
    TGGTCACGAC TCAGGGTTCA CTCACTCTTG TAGAAAAGTCT GGGTCGGTGA ATTGGGATAG GAGCTCCTGC TGACGTCGAG CTGATCACCG AAGGGGTGTG 701 AGGAGTCCCTT TACCATGGCC CAGAGAGCCA CTCCCACTGG GTCCACAGCC CAGGCTGAATG CACAGAGCTG GACCTGCAAA AGTTTCCAG
    TCCTCAGGGAA ATGGTACCGG AGGACGTGGA GTCTCTCGGT GAGGGTGACC CAGGTGTCGG GGTAGCTTAC GTGTCTCGAC CTGGACGTTT TCAAAGGTC 801 CTCTGCCTCC TATACTGGAG CTGAGACCTT GGGGGGAAAC ACAGTCGAAA GCACTGGAGA CAGGCTGGAG CTCAATGTGC CCTTTGAAGT TCCCAGCCCT
    GAGACGGAGG ATATGACCTC GACTCTGGAA CCCCCCTTTG TGTCAGCTTT CGTGACCTCT GTCCGACCTC GAGTTACACG GGAAACTTCA AGGGTCGGGA

901 TAAGC
    ATTCG
```

FIG._1

```
        10         20         30         40         50
         |          |          |          |          |
MDCQENEYWDQWGRCVTCQRCGPGQELSKDCGYGEGGDAYCTACPPRRYK 60         70         80         90        100
         |          |          |          |          |
SSWGHHRCQSCITCAVINRVQKVNCTATSNAVCGDCLPRFYRKTRIGGLQ 110        120        130        140        150
         |          |          |          |          |
DQECIPCTKQTPTSEVQCAFQLSLVEADAPTVPPQEATLVALVSSLLVVF 160        170        180        190        200
         |          |          |          |          |
TLAFLGLFFLYCKQFFNRHCQRVTGGLLQFEADKTAKEESLFPVPPSKET 210        220        230        240        250
         |          |          |          |          |
SAESQVSENIFQTQPLNPILEDDCSSTSGFPTQESFTMASCTSESHSHWV 260        270        280        290
         |          |          |          |
HSPIECTELDLQKFSSSASYTGAETLGGNTVESTGDRLELNVPFEVPSP
```

FIG._2

```
        10         20         30         40         50
         |          |          |          |          |
MDCQENEYWDQWGRCVTCQRCGPGQELSKDCGYGEGGDAYCTACPPRRYK 60         70         80         90        100
         |          |          |          |          |
SSWGHHRCQSCITCAVINRVQKVNCTATSNAVCGDCLPRFYRKTRIGGLQ 110        120        130        140        150
         |          |          |          |          |
DQECIPCTKQTPTSEVQCAFQLSLVEADAPTVPPQEATLVALVSSLLVVF 160        170        180        190        200
         |          |          |          |          |
TLAFLGLFFLYCKQFFNRHCQRGGLLQFEADKTAKEESLFPVPPSKETSA 210        220        230        240        250
         |          |          |          |          |
ESQVSENIFQTQPLNPILEDDCSSTSGFPTQESFTMASCTSESHSHWVHS 260        270        280        290
         |          |          |          |
PIECTELDLQKFSSSASYTGAETLGGNTVESTGDRLELNVPFEVPSP
```

FIG._4

```
  1 ACCATGGATT GCCAAGAAAA TGAGTACTGG GACCAATGGG GACGGTGTGT CACCCTGCCAA CGGTGTGGTC CTGGACAGGA GCTATCCAAG GATTGTGGTT
    TGGTACCTAA CGGTTCTTTT ACTCATGACC CTGGTTACCC GCCACACCAG GTGGACGGTT GCCACACCAG GACCTGTCCT CGATAGGTTC CTAACACCAA
    ^ORF starts here
                          ^cysteine-rich repeat 1

101 ATGGAGAGGG TGGAGATGCC TACTGCACAG CCTGCCCTCC TCGCAGGTAC GGGGCCACCA CAGATGTCAG AGTTGCATCA CCTGTGCTGT
    TACCCTCTCCC ACCTCTACGG ATGACGTGTC GGACGGGAGG AGCGTCCATG CCCCGGTGGT GTCTACAGTC TCAACGTAGT GGACACGACA
                                                           ^cysteine-rich repeat 2

201 CATCAATCGT GTTCAGAAGG TCAACTGCAC AGCTACCTCT AATGCTGTCT GTGGGGACTG TTTGCCCAGG TTCTACCGAA AGACACGCAT TGGAGGCCTG
    GTAGTTAGCA CAAGTCTTCC AGTTGACGTG TCGATGGAGA TTACGACAGA CACCCCCTGAC AAACGGGTCC AAGATGGCTT TCTGTGCGTA ACCTCCGGAC
                                                          ^cysteine-rich repeat 3

301 CAGGACCAAG AGTGCATCCC GTGCACGAAG CAGACCCCCA CCTCTGAGGT TTCCAGTTGA GCTTAGTGGA GCTTAGTGAC CCCACAGTGC
    GTCCTGGTTC TCACGTAGGG CACGTGCTTC GTCTGGGGGT GGAGACTCCA AGGTCAACT CGAATCACCT CGAATCACTG GGGTGTCACG

401 CCCCTCAGGA GGCCACACTT GTTGCACTGA TGAGCAGCCT GCTAGTGGTG TTTACCCTGG CCTTCCTGGG GCTCTTCTTC CTCTACTGCA AGCAGTTCTT
    GGGGAGTCCT CCGGTGTGAA CAACGTGACT ACTCGTCGGA CGATCACCAC AAATGGGACC GGAAGGACCC CGAGAAGAAG GAGATGACGT TCGTCAAGAA
                        ^transmembrane domain 501 CAACAGACAT TGCCAGCGTG GAGGTTTGCT GCAGTTTGAG GCTGATAAAA CAGCAAAAGA GGAATCTCTC TTCCCCGTGC CACCCAGCAA GGAGACCAGT
    GTTGTCTGTA ACGGTCGCAC CTCCAAACGA CGTCAAACTC CGACTATTTT GTCGTTTCCT CCTTAGAGAG AAGGGGCACG GTGGGTCGTT CCTCTGGTCA 601 GCTGAGTCCC AAGTGAGTGA GAACATCTTT CAGACCCAGC CACTTAACCC TATCCTCGAG GACGACTGCA GCTCGACTAG TGGCTTCCCC ACACAGGAGT
    CGACTCAGGG TTCACTCACT CTTGTAGAAA GTCTGGGTCG GTGAATTGGG ATAGGAGCTC CTGCTGACGT CGAGCTGATC ACCGAAGGGG TGTGTCCTCA 701 CCTTTACCAT GGCCTCCTGC ACCTCAGAGA GCCACTCCCA CTGGGTCCAC AGCCCCATCG AATGCACAGA GCTGGACCTG CAAAAGTTTT CCAGCTCTGC
    GGAAATGGTA CCGGAGGACG TGGAGTCTCT CGGTGAGGGT GACCCAGGTG TCGGGGTAGC TTACGTGTCT CGACCTGGAC GTTTTCAAAA GGTCGAGACG 801 CTCCTATACT GGAGCTGAGA CCTTGGGGGG AAACACAGTC GAAAGCACTG GAGACAGGCT GGAGCTCAAT GTGCCCCTTTG AAGTTCCCAG CCCTTAAGC
    GAGGATATGA CCTCGACTCT GGAACCCCCC TTTGTGTCAG CTTTCGTGAC CTCTGTCCGA CCTCGAGTTA CACGGGGAAAC TTCAAGGGTC GGGAATTCG
```

FIG._3

```
<297 matches in an overlap of 299: 99.33 percent similarity
<gaps in first sequence: 1 (2 residues), gaps in second sequence: 0
<score: 1598 (Dayhoff PAM 250 matrix, gap penalty = 8 + 4 per residue)
<endgaps not penalized
```

```
                    10        20        30        40        50
DNA101848   MDCQENEYWDQWGRCVTCQRCGPGQELSKDCGYGEGGDAYCTACPPRRYK
            **************************************************
DNA98853    MDCQENEYWDQWGRCVTCQRCGPGQELSKDCGYGEGGDAYCTACPPRRYK
                    10        20        30        40        50

60        70        80        90       100
DNA101848   SSWGHHRCQSCITCAVINRVQKVNCTATSNAVCGDCLPRFYRKTRIGGLQ
            **************************************************
DNA98853    SSWGHHRCQSCITCAVINRVQKVNCTATSNAVCGDCLPRFYRKTRIGGLQ
                    60        70        80        90       100

110       120       130       140       150
DNA101848   DQECIPCTKQTPTSEVQCAFQLSLVEADAPTVPPQEATLVALVSSLLVVF
            **************************************************
DNA98853    DQECIPCTKQTPTSEVQCAFQLSLVEADAPTVPPQEATLVALVSSLLVVF
                   110       120       130       140       150

160       170       180       190
DNA101848   TLAFLGLFFLYCKQFFNRHCQR--GGLLQFEADKTAKEESLFPVPPSKET
            **********************  **************************
DNA98853    TLAFLGLFFLYCKQFFNRHCQRVTGGLLQFEADKTAKEESLFPVPPSKET
                   160       170       180       190       200

200       210       220       230       240
DNA101848   SAESQVSENIFQTQPLNPILEDDCSSTSGFPTQESFTMASCTSESHSHWV
            **************************************************
DNA98853    SAESQVSENIFQTQPLNPILEDDCSSTSGFPTQESFTMASCTSESHSHWV
                   210       220       230       240       250

250       260       270       280       290
DNA101848   HSPIECTELDLQKFSSSASYTGAETLGGNTVESTGDRLELNVPFEVPSP
            *************************************************
DNA98853    HSPIECTELDLQKFSSSASYTGAETLGGNTVESTGDRLELNVPFEVPSP
                   260       270       280       290
```

FIG._5

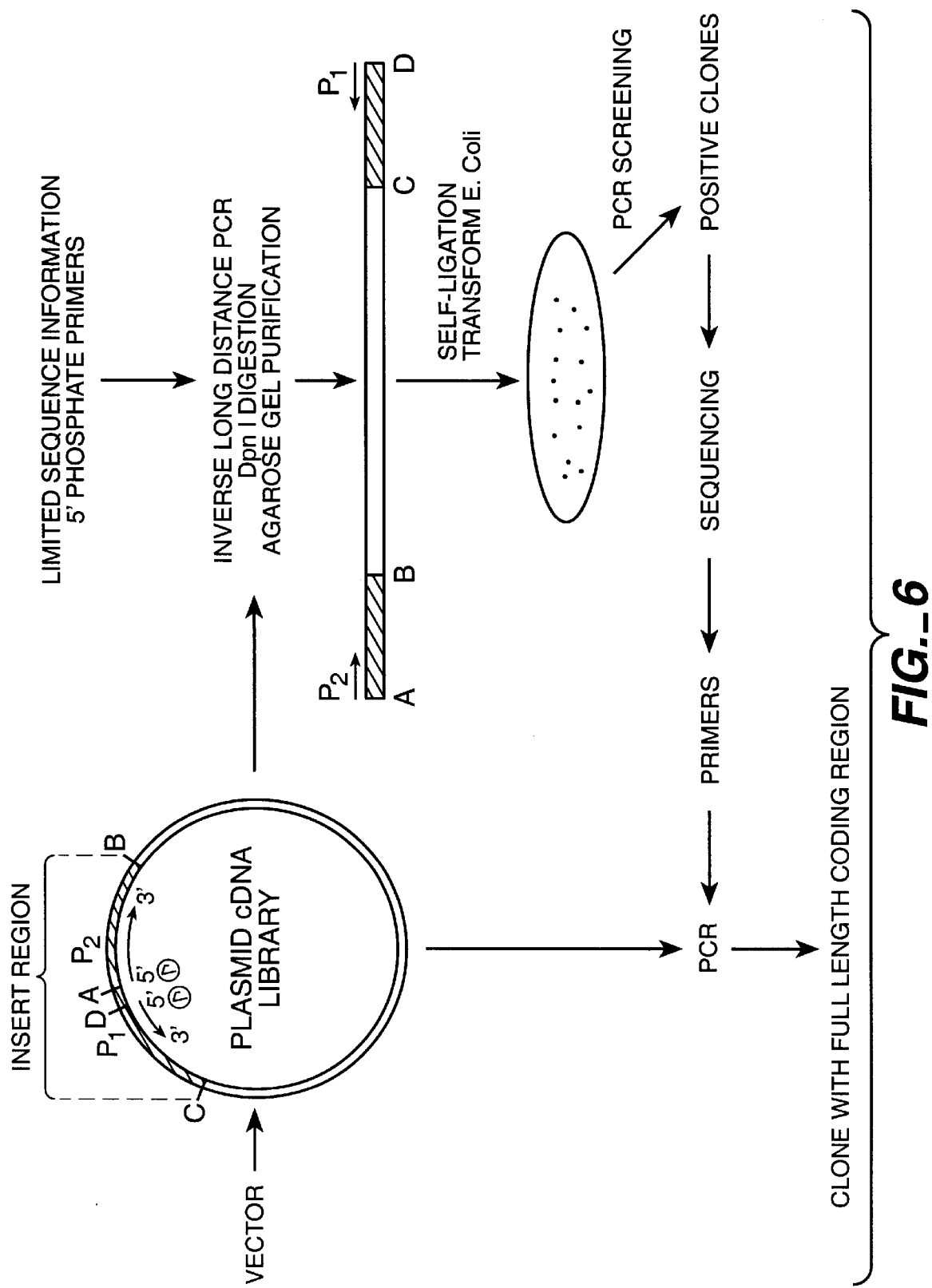
FIG._6

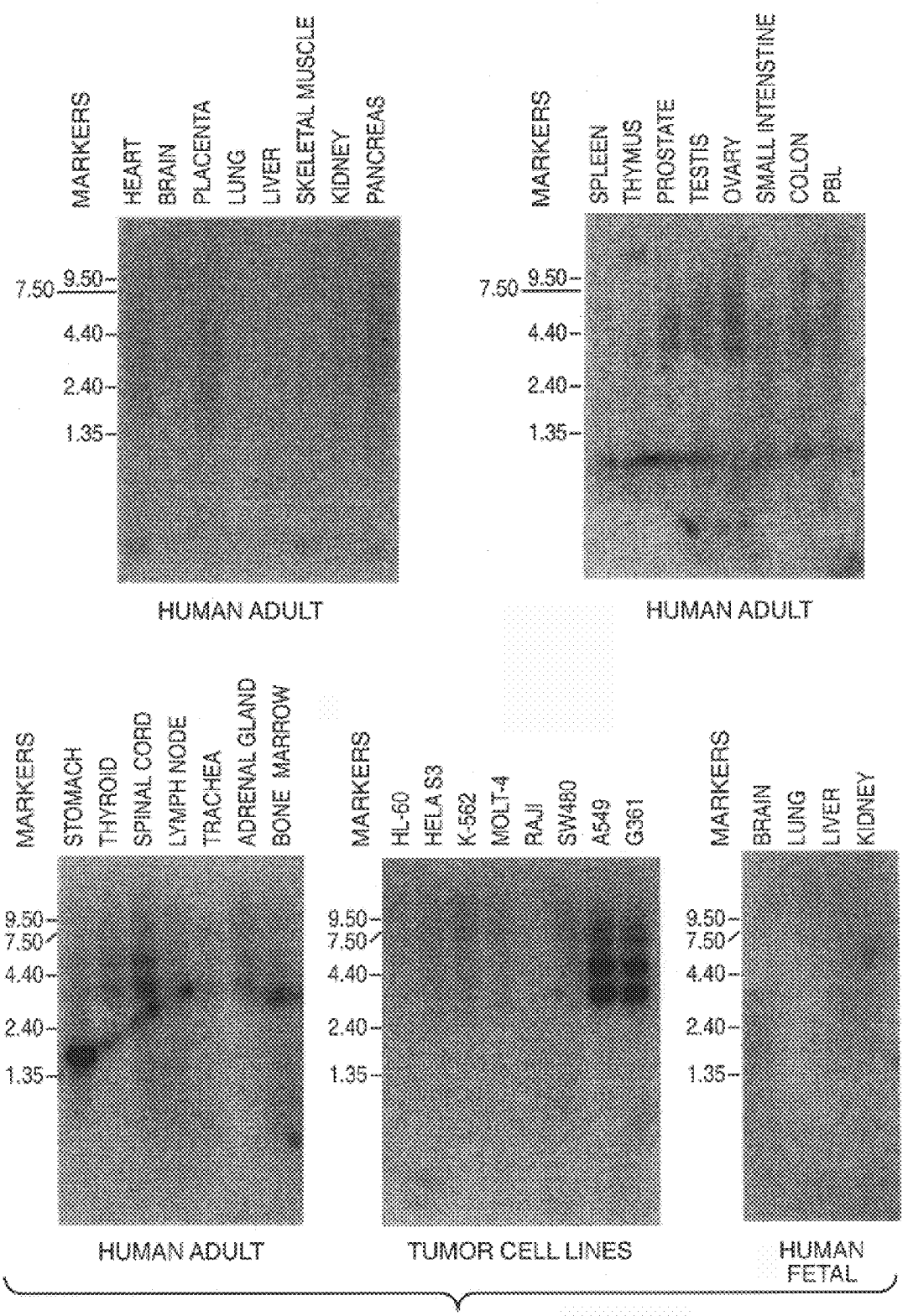
FIG._7

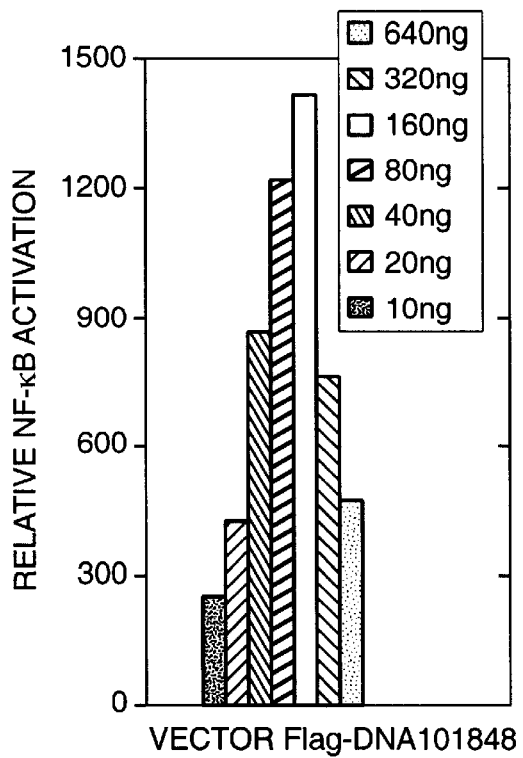
FIG._8A
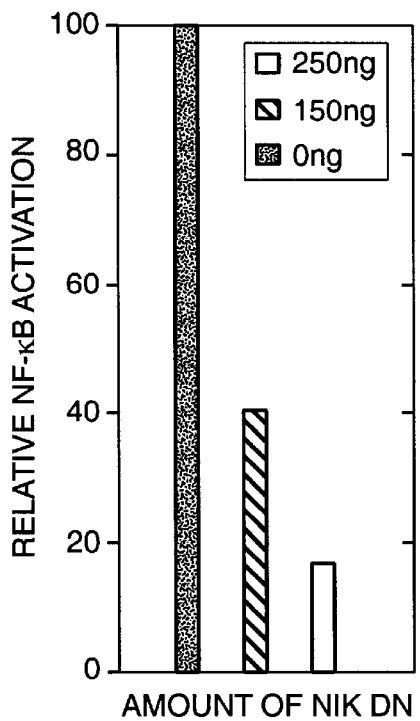
FIG._8B
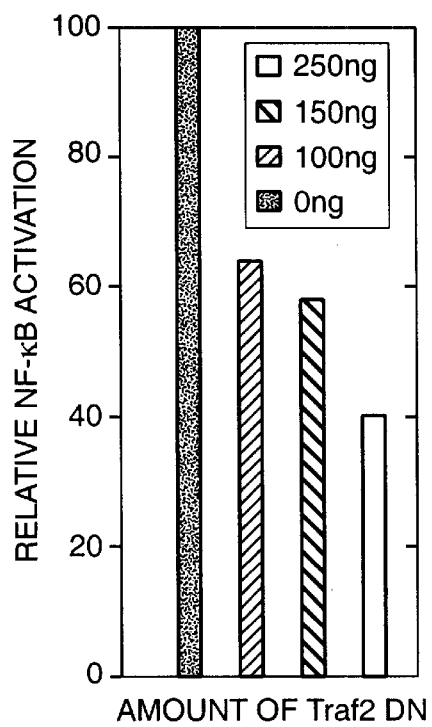
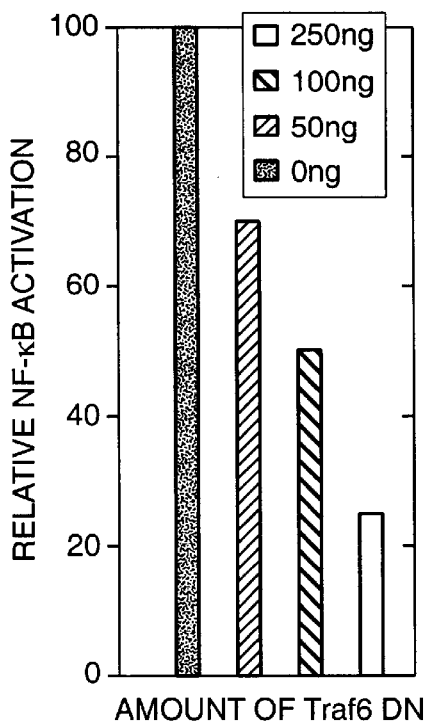
FIG._8C

```
  1 GGAGGGGGCT GGGTGAGATG TGTGCTCTGC GCTGAGGTGG ATTTGTACCG GAGTCCCATT TGGGAGCAAG AGCCATCTAC TCGTCCGTTA CCGGCCTTCC
    CCTCCCCCGA CCCACTCTAC ACACGAGACG CGACTCCACC TAAACATGGC CTCAGGGTAA ACCCTCGTTC TCGGTAGATG AGCAGGCAAT GGCCGGAAGG
                         ^forward primer 509-1                                                          ^left primer 1: 509-p5

101 CACCATGGAT TGCCAAGAAA ATGAGTACTG GGACCAATGG GGACGGTGTG TCACCTGCCA ACGGTGTGGT CCTGGACAGG AGCTATCCAA GGATTGTGGT
    GTGGTACCTA ACGGTTCTTT TACTCATGAC CCTGGTTACC CCTGCCACAC AGTGGACGGT TGCCACACCA GGACCTGTCC TCGATAGGTT CCTAACACCA
                                                ^right primer 2: 509-p6

201 TATGGAGAGG GTGGAGATGC CTACTGCACA GCCTGCCCTC CTCGCAGGTA CAAAAGCAGC TGGGGCCACC ACAAATGTCA GAGTTGCATC AC
    ATACCTCTCC CACCTCTACG GATGACGTGT CGGACGGGAG GAGCGTCCAT GTTTTCGTCG ACCCCGGTGG TGTTTACAGT CTCAACGTAG TG
                                                            ^reverse primer 509-4AS
```

FIG._9

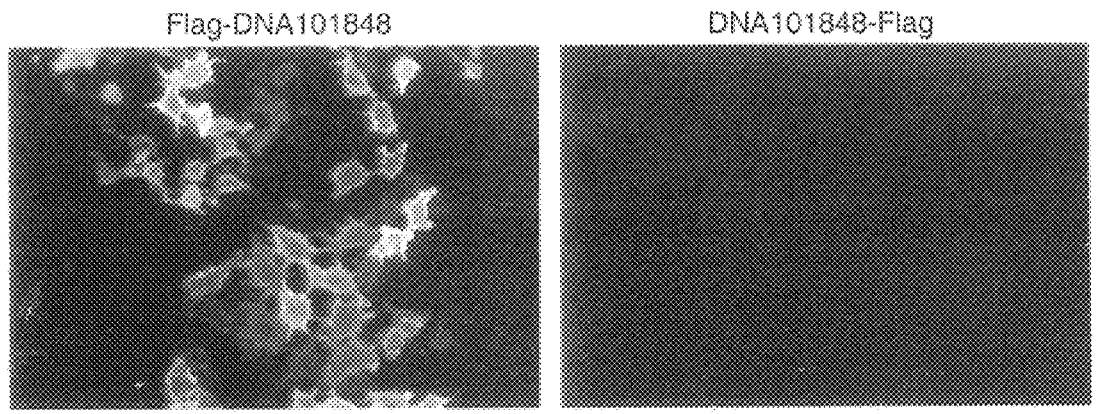
FIG._10A  FIG._10B
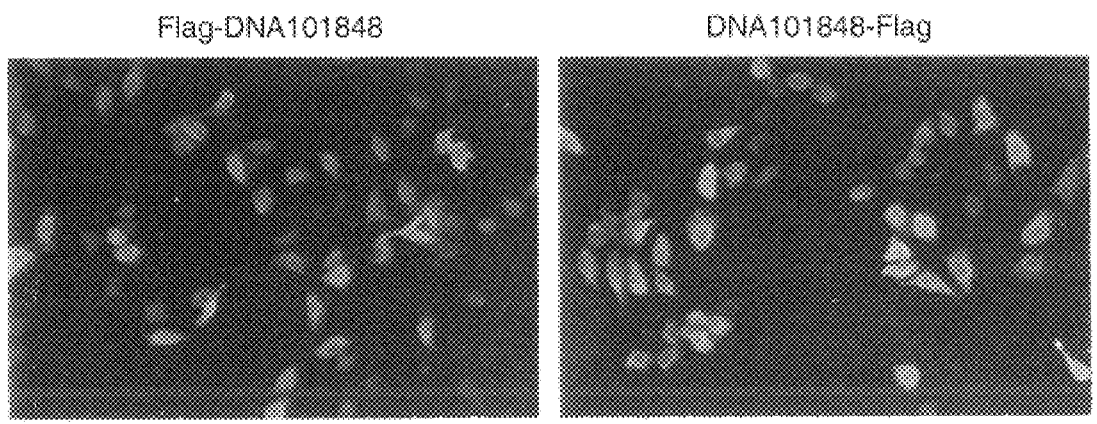
FIG._10C  FIG._10D

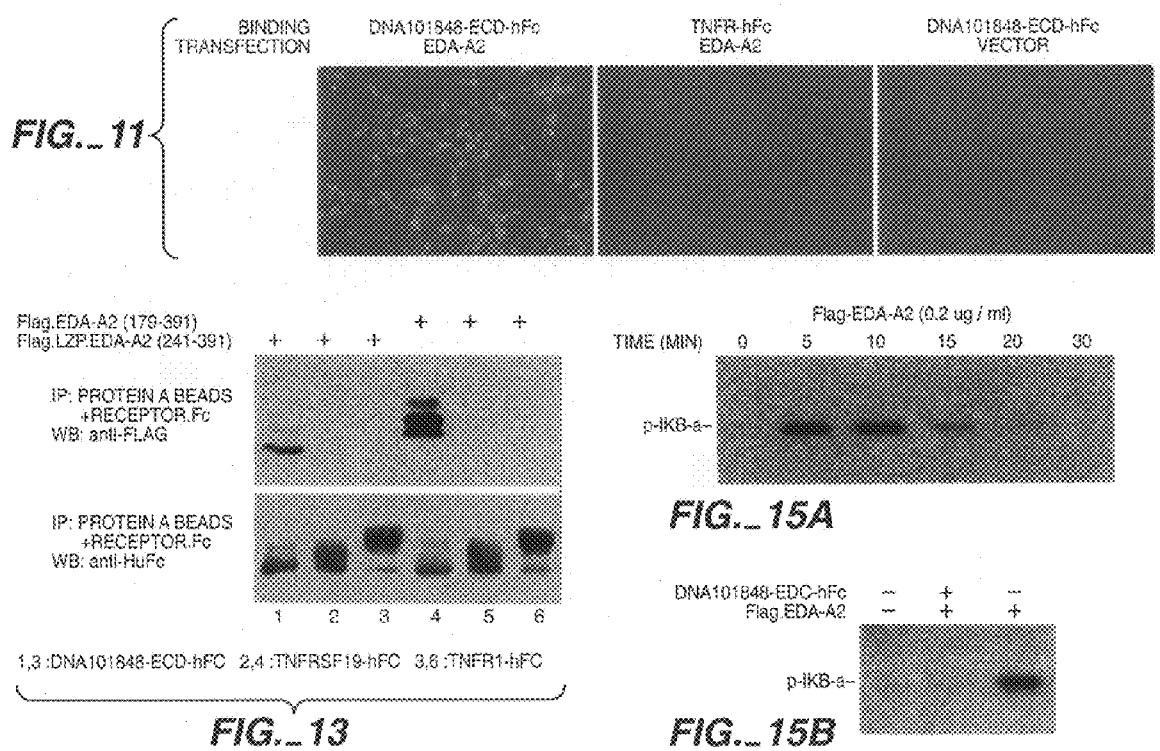

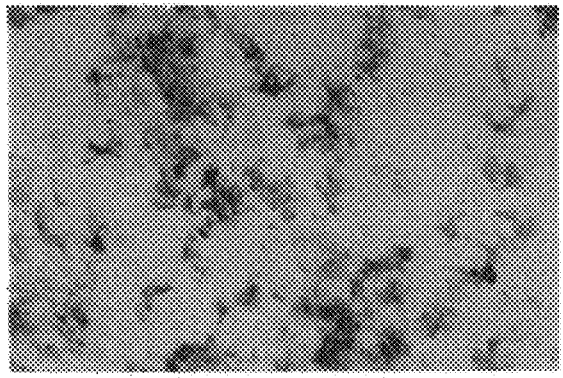
FIG._12A
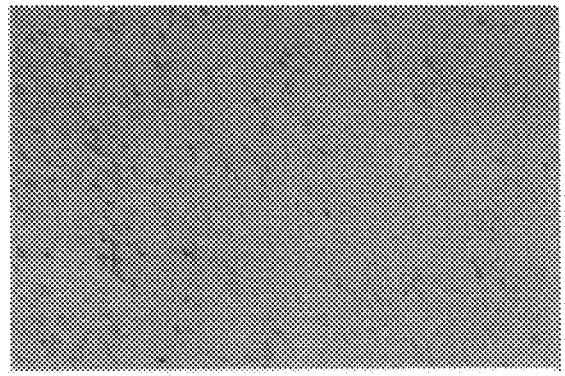
FIG._12B
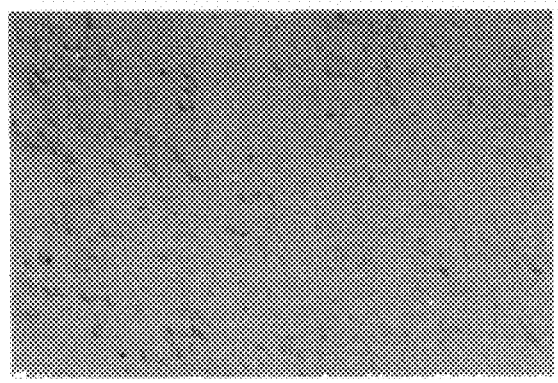
FIG._12C
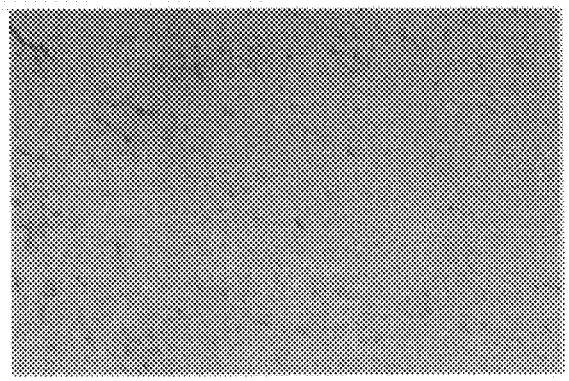
FIG._12D

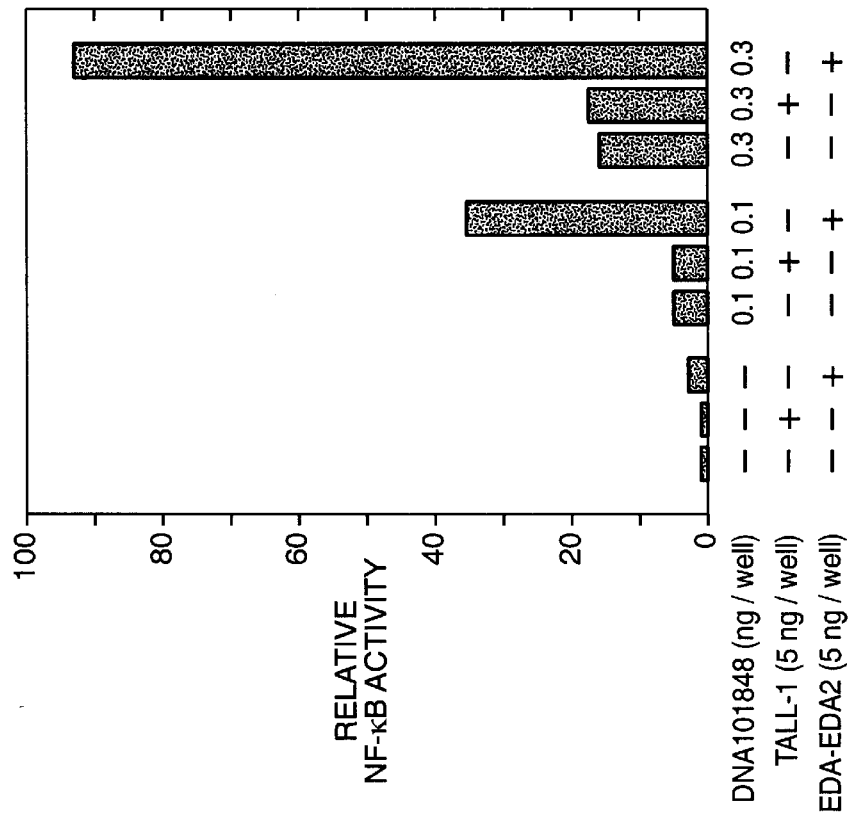
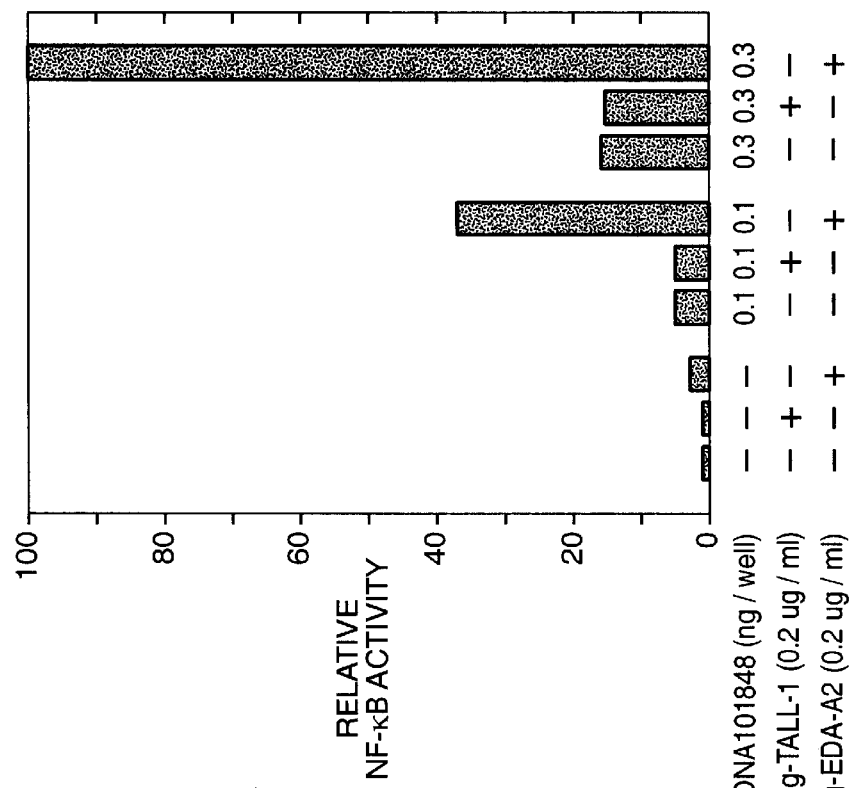

SEQUENCE LISTING

<160> NUMBER OF SEQ ID NOS: 13

<210> SEQ ID NO 1
<211> LENGTH: 905
<212> TYPE: DNA
<213> ORGANISM: Human

<400> SEQUENCE: 1

```
accatggatt gccaagaaaa tgagtactgg gaccaatggg gacggtgtgt          50
cacctgccaa cggtgtggtc ctggacagga gctatccaag gattgtggtt         100
atggagaggg tggagatgcc tactgcacag cctgccctcc tcgcaggtac         150
aaaagcagct ggggccacca cagatgtcag agttgcatca cctgtgctgt         200
catcaatcgt gttcagaagg tcaactgcac agctacctct aatgctgtct         250
gtggggactg tttgcccagg ttctaccgaa agacacgcat tggaggcctg         300
caggaccaag agtgcatccc gtgcacgaag cagaccccca cctctgaggt         350
tcaatgtgcc ttccagttga gcttagtgga ggcagatgca cccacagtgc         400
cccctcagga ggccacactt gttgcactgg tgagcagcct gctagtggtg         450
tttaccctgg ccttcctggg gctcttcttc ctctactgca agcagttctt         500
caacagacat tgccagcgtg ttacaggagg tttgctgcag tttgaggctg         550
ataaaacagc aaaggaggaa tctctcttcc ccgtgccacc cagcaaggag         600
accagtgctg agtcccaagt gagtgagaac atctttcaga cccagccact         650
taaccctatc ctcgaggacg actgcagctc gactagtggc ttccccacac         700
aggagtcctt taccatggcc tcctgcacct cagagagcca ctcccactgg         750
gtccacagcc ccatcgaatg cacagagctg gacctgcaaa agtttttccag        800 ctctgcctcc tatactggag ctgagaccctt gggggggaaac acagtcgaaa       850 gcactggaga caggctggag ctcaatgtgc cctttgaagt tcccagccct         900
taagc                                                          905
```

<210> SEQ ID NO 2
<211> LENGTH: 905
<212> TYPE: DNA

-continued

<213> ORGANISM: Human

<400> SEQUENCE: 2

| | |
|---|---:|
| gcttaagggc tgggaacttc aaagggcaca ttgagctcca gcctgtctcc | 50 |
| agtgctttcg actgtgtttc ccccaaggt ctcagctcca gtataggagg | 100 |
| cagagctgga aaactttgc aggtccagct ctgtgcattc gatggggctg | 150 |
| tggacccagt gggagtggct ctctgaggtg caggaggcca tggtaaagga | 200 |
| ctcctgtgtg gggaagccac tagtcgagct gcagtcgtcc tcgaggatag | 250 |
| ggttaagtgg ctgggtctga agatgttct cactcacttg ggactcagca | 300 |
| ctggtctcct tgctgggtgg cacggggaag agagattcct cctttgctgt | 350 |
| tttatcagcc tcaaactgca gcaaacctcc tgtaacacgc tggcaatgtc | 400 |
| tgttgaagaa ctgcttgcag tagaggaaga agagccccag gaaggccagg | 450 |
| gtaaacacca ctagcaggct gctcaccagt gcaacaagtg tggcctcctg | 500 |
| agggggcact gtgggtgcat ctgcctccac taagctcaac tggaaggcac | 550 |
| attgaacctc agaggtgggg gtctgcttcg tgcacgggat gcactcttgg | 600 |
| tcctgcaggc ctccaatgcg tgtctttcgg tagaacctgg gcaaacagtc | 650 |
| cccacagaca gcattagagg tagctgtgca gttgaccttc tgaacacgat | 700 |
| tgatgacagc acaggtgatg caactctgac atctgtggtg gccccagctg | 750 |
| cttttgtacc tgcgaggagg gcaggctgtg cagtaggcat ctccaccctc | 800 |
| tccataacca caatccttgg atagctcctg tccaggacca caccgttggc | 850 |
| aggtgacaca ccgtccccat tggtcccagt actcattttc ttggcaatcc | 900 |
| atggt | 905 |

<210> SEQ ID NO 3
<211> LENGTH: 299
<212> TYPE: PRT
<213> ORGANISM: Human

<400> SEQUENCE: 3

```
Met Asp Cys Gln Glu Asn Glu Tyr Trp Asp Gln Trp Gly Arg Cys
 1               5                  10                  15

Val Thr Cys Gln Arg Cys Gly Pro Gly Gln Glu Leu Ser Lys Asp
                20                  25                  30

Cys Gly Tyr Gly Glu Gly Gly Asp Ala Tyr Cys Thr Ala Cys Pro
                35                  40                  45

Pro Arg Arg Tyr Lys Ser Ser Trp Gly His His Arg Cys Gln Ser
                50                  55                  60

Cys Ile Thr Cys Ala Val Ile Asn Arg Val Gln Lys Val Asn Cys
                65                  70                  75

Thr Ala Thr Ser Asn Ala Val Cys Gly Asp Cys Leu Pro Arg Phe
                80                  85                  90

Tyr Arg Lys Thr Arg Ile Gly Gly Leu Gln Asp Gln Glu Cys Ile
                95                 100                 105

Pro Cys Thr Lys Gln Thr Pro Thr Ser Glu Val Gln Cys Ala Phe
               110                 115                 120

Gln Leu Ser Leu Val Glu Ala Asp Ala Pro Thr Val Pro Pro Gln
               125                 130                 135

Glu Ala Thr Leu Val Ala Leu Val Ser Ser Leu Leu Val Val Phe
               140                 145                 150
```

Thr Leu Ala Phe Leu Gly Leu Phe Phe Leu Tyr Cys Lys Gln Phe
          155                 160                 165

Phe Asn Arg His Cys Gln Arg Val Thr Gly Gly Leu Leu Gln Phe
          170                 175                 180

Glu Ala Asp Lys Thr Ala Lys Glu Glu Ser Leu Phe Pro Val Pro
          185                 190                 195

Pro Ser Lys Glu Thr Ser Ala Glu Ser Gln Val Ser Glu Asn Ile
          200                 205                 210

Phe Gln Thr Gln Pro Leu Asn Pro Ile Leu Gly Asp Asp Cys Ser
          215                 220                 225

Ser Thr Ser Gly Phe Pro Thr Gln Glu Ser Phe Thr Met Ala Ser
          230                 235                 240

Cys Thr Ser Glu Ser His Ser His Trp Val His Ser Pro Ile Glu
          245                 250                 255

Cys Thr Glu Leu Asp Leu Gln Lys Phe Ser Ser Ser Ala Ser Tyr
          260                 265                 270

Thr Gly Ala Glu Thr Leu Gly Gly Asn Thr Val Glu Ser Thr Gly
          275                 280                 285

Asp Arg Leu Glu Leu Asn Val Pro Phe Glu Val Pro Ser Pro
          290                 295             299

<210> SEQ ID NO 4
<211> LENGTH: 899
<212> TYPE: DNA
<213> ORGANISM: Human

<400> SEQUENCE: 4
accatggatt gccaagaaaa tgagtactgg gaccaatggg gacggtgtgt       50
cacctgccaa cggtgtggtc ctggacagga gctatccaag gattgtggtt      100
atggagaggg tggagatgcc tactgcacag cctgccctcc tcgcaggtac      150
aaaagcagct ggggccacca cagatgtcag agttgcatca cctgtgctgt      200
catcaatcgt gttcagaagg tcaactgcac agctacctct aatgctgtct      250
gtggggactg tttgcccagg ttctaccgaa agacacgcat ggaggcctg       300 caggaccaag agtgcatccc gtgcacgaag cagacccca cctctgaggt       350 tcaatgtgcc ttccagttga gcttagtgga ggcagatgca cccacagtgc      400
cccctcagga ggccacactt gttgcactgg tgagcagcct gctagtggtg      450
tttaccctgg ccttcctggg gctcttcttc ctctactgca agcagttctt      500
caacagacat tgccagcgtg gaggtttgct gcagtttgag gctgataaaa      550
cagcaaagga ggaatctctc ttccccgtgc cacccagcaa ggagaccagt      600
gctgagtccc aagtgagtga aacatcttt cagacccagc cacttaaccc       650
tatcctcgag gacgactgca gctcgactag tggcttcccc acacaggagt      700
cctttaccat ggcctcctgc acctcagaga gccactccca ctgggtccac      750
agccccatcg aatgcacaga gctggacctg caaaagtttt ccagctctgc      800
ctcctatact ggagctgaga ccttgggggg aaacacagtc gaaagcactg      850
gagacaggct ggagctcaat gtgccctttg aagttcccag cccttaagc      899

<210> SEQ ID NO 5
<211> LENGTH: 899
<212> TYPE: DNA

-continued

<210> SEQ ID NO 5
<211> LENGTH: 899
<212> TYPE: DNA
<213> ORGANISM: Human

<400> SEQUENCE: 5

```
gcttaagggc tgggaacttc aaagggcaca ttgagctcca gcctgtctcc        50
agtgctttcg actgtgtttc cccccaaggt ctcagctcca gtataggagg       100
cagagctgga aaacttttgc aggtccagct ctgtgcattc gatggggctg       150
tggacccagt gggagtggct ctctgaggtg caggaggcca tggtaaagga       200
ctcctgtgtg gggaagccac tagtcgagct gcagtcgtcc tcgaggatag       250
ggttaagtgg ctgggtctga agatgttct cactcacttg ggactcagca        300
ctggtctcct tgctgggtgg cacggggaag agagattcct cctttgctgt       350
tttatcagcc tcaaactgca gcaaacctcc acgctggcaa tgtctgttga       400
agaactgctt gcagtagagg aagaagagcc ccaggaaggc cagggtaaac       450
accactagca ggctgctcac cagtgcaaca agtgtggcct cctgagggg        500
cactgtgggt gcatctgcct ccactaagct caactggaag gcacattgaa       550
cctcagaggt gggggtctgc ttcgtgcacg ggatgcactc ttggtcctgc       600
aggcctccaa tgcgtgtctt tcggtagaac ctgggcaaac agtccccaca       650
gacagcatta gaggtagctg tgcagttgac cttctgaaca cgattgatga       700
cagcacaggt gatgcaactc tgacatctgt ggtggcccca gctgcttttg       750
tacctgcgag gagggcaggc tgtgcagtag gcatctccac cctctccata       800
accacaatcc ttggatagct cctgtccagg accacaccgt tggcaggtga       850
cacaccgtcc ccattggtcc cagtactcat tttcttggca atccatggt        899
```

<210> SEQ ID NO 6
<211> LENGTH: 297
<212> TYPE: PRT
<213> ORGANISM: Human

<400> SEQUENCE: 6

```
Met Asp Cys Gln Glu Asn Glu Tyr Trp Asp Gln Trp Gly Arg Cys
  1               5                  10                  15

Val Thr Cys Gln Arg Cys Gly Pro Gly Gln Glu Leu Ser Lys Asp
                 20                  25                  30

Cys Gly Tyr Gly Glu Gly Gly Asp Ala Tyr Cys Thr Ala Cys Pro
                 35                  40                  45

Pro Arg Arg Tyr Lys Ser Ser Trp Gly His His Arg Cys Gln Ser
                 50                  55                  60

Cys Ile Thr Cys Ala Val Ile Asn Arg Val Gln Lys Val Asn Cys
                 65                  70                  75

Thr Ala Thr Ser Asn Ala Val Cys Gly Asp Cys Leu Pro Arg Phe
                 80                  85                  90

Tyr Arg Lys Thr Arg Ile Gly Gly Leu Gln Asp Gln Glu Cys Ile
                 95                 100                 105

Pro Cys Thr Lys Gln Thr Pro Thr Ser Glu Val Gln Cys Ala Phe
                110                 115                 120

Gln Leu Ser Leu Val Glu Ala Asp Ala Pro Thr Val Pro Pro Gln
                125                 130                 135

Glu Ala Thr Leu Val Ala Leu Val Ser Ser Leu Leu Val Val Phe
                140                 145                 150

Thr Leu Ala Phe Leu Gly Leu Phe Phe Leu Tyr Cys Lys Gln Phe
```

```
                    155                 160                 165
Phe Asn Arg His Cys Gln Arg Gly Gly Leu Leu Gln Phe Glu Ala
                170                 175                 180
Asp Lys Thr Ala Lys Glu Glu Ser Leu Phe Pro Val Pro Pro Ser
                185                 190                 195
Lys Glu Thr Ser Ala Glu Ser Gln Val Ser Glu Asn Ile Phe Gln
                200                 205                 210
Thr Gln Pro Leu Asn Pro Ile Leu Glu Asp Asp Cys Ser Ser Thr
                215                 220                 225
Ser Gly Phe Pro Thr Gln Glu Ser Phe Thr Met Ala Ser Cys Thr
                230                 235                 240
Ser Glu Ser His Ser His Trp Val His Ser Pro Ile Glu Cys Thr
                245                 250                 255
Glu Leu Asp Leu Gln Lys Phe Ser Ser Ser Ala Ser Tyr Thr Gly
                260                 265                 270
Ala Glu Thr Leu Gly Gly Asn Thr Val Glu Ser Thr Gly Asp Arg
                275                 280                 285
Leu Glu Leu Asn Val Pro Phe Glu Val Pro Ser Pro
                290                 295     297

<210> SEQ ID NO 7
<211> LENGTH: 292
<212> TYPE: DNA
<213> ORGANISM: Human

<400> SEQUENCE: 7
ggagggggct gggtgagatg tgtgctctgc gctgaggtgg atttgtaccg           50
gagtcccatt tgggagcaag agccatctac tcgtccgtta ccggccttcc          100
caccatggat tgccaagaaa atgagtactg ggaccaatgg ggacggtgtg          150
tcacctgcca acggtgtggt cctggacagg agctatccaa ggattgtggt          200
tatggagagg gtggagatgc ctactgcaca gcctgccctc ctcgcaggta          250
caaaagcagc tggggccacc acaaatgtca gagttgcatc ac                 292

<210> SEQ ID NO 8
<211> LENGTH: 21
<212> TYPE: DNA
<213> ORGANISM: Artificial
<220> FEATURE:
<221> NAME/KEY: Artificial sequence
<222> LOCATION: 1-21
<223> OTHER INFORMATION: Sequence is synthesized.

<400> SEQUENCE: 8
gagggggctg ggtgagatgt g                                         21

<210> SEQ ID NO 9
<211> LENGTH: 22
<212> TYPE: DNA
<213> ORGANISM: Artificial
<220> FEATURE:
<221> NAME/KEY: Artificial sequence
<222> LOCATION: 1-22
<223> OTHER INFORMATION: Sequence is synthesized.

<400> SEQUENCE: 9
tgcttttgta cctgcgagga gg                                        22

<210> SEQ ID NO 10
```

-continued

```
<211> LENGTH: 22
<212> TYPE: DNA
<213> ORGANISM: Artificial
<220> FEATURE:
<221> NAME/KEY: Artificial sequence
<222> LOCATION: 1-22
<223> OTHER INFORMATION: Sequence is synthesized.

<400> SEQUENCE: 10
catggtggga aggccggtaa cg                                              22

<210> SEQ ID NO 11
<211> LENGTH: 28
<212> TYPE: DNA
<213> ORGANISM: Artificial
<220> FEATURE:
<221> NAME/KEY: Artificial Sequence
<222> LOCATION: 1-28
<223> OTHER INFORMATION: Sequence is synthesized.

<400> SEQUENCE: 11
gattgccaag aaaatgagta ctgggacc                                        28

<210> SEQ ID NO 12
<211> LENGTH: 35
<212> TYPE: DNA
<213> ORGANISM: Artificial
<220> FEATURE:
<221> NAME/KEY: Artificial sequence
<222> LOCATION: 1-35
<223> OTHER INFORMATION: Sequence is synthesized.

<400> SEQUENCE: 12
ggaggatcga taccatggat tgccaagaaa atgag                                35

<210> SEQ ID NO 13
<211> LENGTH: 41
<212> TYPE: DNA
<213> ORGANISM: Artificial
<220> FEATURE:
<221> NAME/KEY: Artificial sequence
<222> LOCATION: 1-41
<223> OTHER INFORMATION: Sequence is synthesized.

<400> SEQUENCE: 13
ggaggagcgg ccgcttaagg gctgggaact tcaaagggca c                         41
```

US 6,534,061 B1

TUMOR NECROSIS FACTOR RECEPTOR HOMOLOGS AND NUCLEIC ACIDS ENCODING THE SAME

RELATED APPLICATIONS

This is a non-provisional application claiming priority under Section 119(e) to provisional application number 60/128,849 filed Apr. 12, 1999, now abandoned, the entire disclosure of which is hereby incorporated by reference.

FIELD OF THE INVENTION

The present invention relates generally to the identification and isolation of novel DNA and to the recombinant production of novel polypeptides having homology to tumor necrosis factor receptors, designated herein as "DNA98853" polypeptides and "DNA101848" polypeptides.

BACKGROUND OF THE INVENTION

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., *Bio/Technology*, 12:487–493 (1994); Steller et al., *Science*, 267:1445–1449 (1995)]. Apoptotic cell death naturally occurs in many physiologica processes, including embryonic development and clonal selection in the immune system [Itoh et al., *Cell*, 66:233–243 (1991)]. Decreased levels of apoptotic cell death have been associated with a variety of pathological conditions, including cancer, lupus, and herpes virus infection [Thompson, *Science*, 267:1456–1462 (1995)]. Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebellar degeneration, aplastic anemia, myocardial infarction, stroke, reperfusion injury, and toxin-induced liver disease [see, Thompson, supra].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, *Nature*, 356:397–400 (1992); Steller, supra; Sachs et al., *Blood*, 82:15 (1993)]. For instance, they can be triggered by hormonal stimuli, such as glucocorticoid hormones for immature thymocytes, as well as withdrawal of certain growth factors [Watanabe-Fukunaga et al., *Nature*, 356:314–317 (1992)]. Also, some identified oncogenes such as myc, rel, and EIA, and tumor suppressors, like p53, have been reported to have a role in inducing apoptosis. Certain chemotherapy drugs and some forms of radiation have likewise been observed to have apoptosis-inducing activity [Thompson, supra].

Various molecules, such as tumor necrosis factor-α ("TNF-α"), tumor necrosis factor-β ("TNF-β" or "lymphotoxin-α"), lymphotoxin-β ("LT-β"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), EDA and EDA-A2 have been identified as members of the tumor necrosis factor ("TNF") family of cytokines [See, e.g., Gruss and Dower, *Blood*, 85:3378–3404 (1995); Pitti et al., *J. Biol. Chem.*, 271:12687–12690 (1996); Wiley et al., *Immunity*, 3:673–682 (1995); Browning et al., *Cell*, 72:847–856 (1993); Armitage et al. *Nature*, 357:80–82 (1992), WO 97/01633 published Jan. 16, 1997; WO 97/25428 published Jul. 17, 1997; Marsters et al., *Curr. Biol.*, 8:525–528 (1998); Chicheportiche et al., *J. Biol. Chem.*, 272:32401–32410 (1997); Bayes et al., *Human Molecular Genetics*, 7:1661–1669 (1998); Kere et al., *Nature Genetics*, 13:409–416 (1996)]. Among these molecules, TNF-α, TNF-β, CD30 ligand, 4-1BB ligand, Apo-1 ligand, Apo-2 ligand (TRAIL) and Apo-3 ligand (TWEAK) have been reported to be involved in apoptotic cell death. Both TNF-α and TNF-β have been reported to induce apoptotic death in susceptible tumor cells [Schmid et al., *Proc. Natl. Acad. Sci.*, 83:1881 (1986); Dealtry et al., *Eur. J. Immunol.*, 17:689 (1987)]. Zheng et al. have reported that TNF-α is involved in post-stimulation apoptosis of CD8-positive T cells [Zheng et al., *Nature*, 377:348–351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., *Curr. Op. Immunol.*, 6:279–289 (1994); Nagata et al., *Science*, 267:1449–1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., *J. Exp. Med.*, 169:1747–1756 (1989)].

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohlmans et al., *J. Biol. Chem.*, 264:14927–14934 (1989); Brockhaus et al., *Proc. Natl. Acad. Sci.*, 87:3127–3131 (1990); EP 417,563, published Mar. 20, 1991] and human and mouse cDNAs corresponding to both receptor types have been isolated and characterized [Loetscher et al., *Cell*, 61:351 (1990); Schall et al., *Cell*, 61:361 (1990); Smith et al., *Science*, 248:1019–1023 (1990); Lewis et al., *Proc. Natl. Acad. Sci.*, 88:2830–2834 (1991); Goodwin et al., *Mol. Cell. Biol.*, 11:3020–3026 (1991)]. Extensive polymorphisms have been associated with both TNF receptor genes [see, e.g., Takao et al., *Immunogenetics*, 37:199–203 (1993)]. Both TNFRs share the typical structure of cell surface receptors including extracellular, transmembrane and intracellular regions. The extracellular portions of both receptors are found naturally also as soluble TNF-binding proteins [Nophar, Y. et al., *EMBO J.*, 9:3269 (1990); and Kohno, T. et al., *Proc. Natl. Acad. Sci. U.S.A.*, 87:8331 (1990)]. The cloning of recombinant soluble TNF receptors was reported by Hale et al. [*J. Cell. Biochem. Supplement* 15F, 1991, p. 113 (P424)].

The extracellular portion of type 1 and type 2 TNFRs (TNFR1 and TNFR2) contains a repetitive amino acid sequence pattern of four cysteine-rich domains (CRDs) designated 1 through 4, starting from the NH$_2$-terminus. Each CRD is about 40 amino acids long and contains 4 to 6 cysteine residues at positions which are well conserved [Schall et al., supra; Loetscher et al., supra; Smith et al., supra; Nophar et al., supra; Kohno et al., supra]. In TNFR1, the approximate boundaries of the four CRDs are as follows: CRD1—amino acids 14 to about 53; CRD2—amino acids from about 54 to about 97; CRD3—amino acids from about 98 to about 138; CRD4—amino acids from about 139 to about 167. In TNFR2, CRD1 includes amino acids 17 to about 54; CRD2—amino acids from about 55 to about 97; CRD3—amino acids from about 98 to about 140; and CRD4—amino acids from about 141 to about 179 [Banner et al., *Cell*, 73:431–445 (1993)]. The potential role of the CRDs in ligand binding is also described by Banner et al., supra.

A similar repetitive pattern of CRDs exists in several other cell-surface proteins, including the p75 nerve growth factor receptor (NGFR) [Johnson et al., *Cell*, 47:545 (1986); Radeke et al., *Nature*, 325:593 (1987)], the B cell antigen CD40 [Starnenkovic et al., *EMBO J.*, 8:1403 (1989)], the T cell antigen OX40 [Mallelt et al., *EMBO J.*, 9:1063 (1990)] and the Fas antigen [Yonehara et al., supra and Itoh et al., *Cell*, 66:233–243 (1991)]. CRDs are also found in the soluble TNFR (sTNFR)-like T2 proteins of the Shope and myxoma poxviruses [Upton et al., *Virology*, 160:20–30 (1987); Smith et al., *Biochem. Biophys. Res. Commun.*, 176:335 (1991); Upton et al., *Virology*, 184:370 (1991)]. Optimal alignment of these sequences indicates that the positions of the cysteine residues are well conserved. These receptors are sometimes collectively referred to as members of the TNF/NGF receptor superfamily. Recent studies on p75NGFR showed that the deletion of CRD1 [Welcher, A. A. et al., *Proc. Natl. Acad. Sci. USA*, 88:159–163 (1991)] or a 5-amino acid insertion in this domain [Yan, H. and Chao, M. V., *J. Biol. Chem.*, 266:12099–12104 (1991)] had little or no effect on NGF binding [Yan, H. and Chao, M. V., supra]. p75 NGFR contains a proline-rich stretch of about 60 amino acids, between its CRD4 and transmembrane region, which is not involved in NGF binding [Peetre, C. et al., *Eur. J. Haematol.*, 41:414–419 (1988); Seckinger, P. et al., *J. Biol. Chem.*, 264:11966–11973 (1989); Yan, H. and Chao, M. V., supra]. A similar proline-rich region is found in TNFR2 but not in TNFR1.

The TNF family ligands identified to date, with the exception of lymphotoxin-α, are type II transmembrane proteins, whose C-terminus is extracellular. In contrast, most receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the TNFR family have been identified. Such newly identified members of the TNFR family include CAR1, HVEM and osteoprotegerin (OPG) [Brojatsch et al., *Cell*, 87:845–855 (1996); Montgomery et al., *Cell*, 87:427–436 (1996); Marsters et al., *J. Biol. Chem.*, 272:14029–14032 (1997); Simonet et al., *Cell*, 89:309–319 (1997)]. Unlike other known TNFR-like molecules, Simonet et al., supra, report that OPG contains no hydrophobic transmembrane-spanning sequence.

Another new member of the TNF/NGF receptor family has been identified in mouse, a receptor referred to as "GITR" for "glucocorticoid-induced tumor necrosis factor receptor family-related gene" [Nocentini et al., *Proc. Natl. Acad. Sci. USA* 94:6216–6221 (1997)]. The mouse GITR receptor is a 228 amino acid type I transmembrane protein that is expressed in normal mouse T lymphocytes from thymus, spleen and lymph nodes. Expression of the mouse GITR receptor was induced in T lymphocytes upon activation with anti-CD3 antibodies, Con A or phorbol 12-myristate 13-acetate.

In Marsters et al., *Curr. Biol.*, 6:750 (1996), investigators describe a full length native sequence human polypeptide, called Apo-3, which exhibits similarity to the TNFR family in its extracellular cysteine-rich repeats and resembles TNFR1 and CD95 in that it contains a cytoplasmic death domain sequence [see also Marsters et al., *Curr. Biol.*, 6:1669 (1996)]. Apo-3 has also been referred to by other investigators as DR3, wsl-1, TRAMP, and LARD [Chinnaiyan et al., *Science*, 274:990 (1996); Kitson et al., *Nature*, 384:372 (1996); Bodmer et al., *Immunity*, 6:79 (1997); Screaton et al., *Proc. Natl. Acad. Sci.*, 94:4615–4619 (1997)].

Pan et al. have disclosed another TNF receptor family member referred to as "DR4" [Pan et al., *Science*, 276:111–113 (1997)]. The DR4 was reported to contain a cytoplasmic death domain capable of engaging the cell suicide apparatus. Pan et al. disclose that DR4 is believed to be a receptor for the ligand known as Apo-2 ligand or TRAIL.

In Sheridan et al., *Science*, 277:818–821 (1997) and Pan et al., *Science*, 277:815–818 (1997), another molecule believed to be a receptor for the Apo-2 ligand (TRAIL) is described. That molecule is referred to as DR5 (it has also been alternatively referred to as Apo-2; TRAIL-R2, TRICK2 or KILLER [Screaton et al., *Curr. Biol.*, 7:693–696 (1997); Walczak et al., *EMBO J.*, 16:5386–5397 (1997); Wu et al., *Nature Genetics*, 17:141–143 (1997)]. Like DR4, DR5 is reported to contain a cytoplasmic death domain and be capable of signaling apoptosis.

Yet another death domain-containing receptor, DR6, was recently identified [Pan et al., *FEBS Letters*, 431:351–356 (1998)]. Aside from containing four putative extracellular domains and a cytoplasmic death domain, DR6 is believed to contain a putative leucine-zipper sequence that overlaps with a proline-rich motif in the cytoplasmic region. The proline-rich motif resembles sequences that bind to src-homology-3 domains, which are found in many intracellular signal-transducing molecules.

A further group of recently identified receptors are referred to as "decoy receptors," which are believed to function as inhibitors, rather than transducers of signaling. This group includes DCR1 (also referred to as TRID, LIT or TRAIL-R3) [Pan et al., *Science*, 276:111–113 (1997); Sheridan et al., *Science*, 277:818–821 (1997); Mac Farlane et al., *J. Biol. Chem.*, 272:25417–25420 (1997); Schneider et al., *FEBS Letters*, 416:329–334 (1997); Degli-Esposti et al., *J. Exp. Med.*, 186:1165–1170 (1997); and Mongkolsapaya et al., *J. Immunol.*, 160:3–6 (1998)] and DCR2 (also called TRUNDD or TRAIL-R4) [Marsters et al., *Curr. Biol.*, 7:1003–1006 (1997); Pan et al., *FEBS Letters*, 424:41–45 (1998); Degli-Esposti et al., *Immunity*, 7:813–820 (1997)], both cell surface molecules, as well as OPG [Simonet et al., supra] and DCR3 [Pitti et al., *Nature*, 396:699–703 (1998)], both of which are secreted, soluble proteins.

For a review of the TNF family of cytokines and their receptors, see Ashkenazi et al., *Science*, 281:1305–1308 (1998); Golstein, *Curr. Biol.*, 7:R750–R753 (1997); and Gruss and Dower, supra.

As presently understood, the cell death program contains at least three important elements—activators, inhibitors, and effectors; in *C. elegans*, these elements are encoded respectively by three genes, Ced-4, Ced-9 and Ced-3 [Steller, *Science*, 267:1445 (1995); Chinnaiyan et al., *Science*, 275:1122–1126 (1997); Zar et al. *Cell*, 90:405–413 (1997)]. Two of the TNFR family members, TNFR1 and Fas/Apo1 (CD95), can activate apoptotic cell death [Chinnaiyan and Dixit, *Current Biology*, 6:555–562 (1996); Fraser and Evan, *Cell*; 85:781–784 (1996)]. TNFR1 is also known to mediate activation of the transcription factor, NF-KB [Tartaglia et al., *Cell*, 74:845–853 (1993); Hsu et al., *Cell*, 84:299–308 (1996)]. In addition to some ECD homology, these two receptors share homology in their intracellular domain (ICD) in an oligomerization interface known as the death domain [Tartaglia et al., supra; Nagata, *Cell*, 88:355 (1997)]. Death domains are also found in several metazoan proteins that regulate apoptosis, namely, the Drosophila protein, Reaper, and the mammalian proteins referred to as FADD/MORT1, TRADD, and RIP [Cleaveland and Ihle, *Cell*, 81:479–482 (1995)].

Upon ligand binding and receptor clustering, TNFR1 and CD95 are believed to recruit FADD into a death-inducing signaling complex. CD95 purportedly binds FADD directly, while TNFR1 binds FADD indirectly via TRADD [Chinnaiyan et al., *Cell*, 81:505–512 (1995); Boldin et al.,*J. Biol. Chem.*, 270:387–391 (1995); Hsu et al., supra; Chinnaiyan et al., *J. Biol. Chem.*, 271:4961–4965 (1996)]. It has been reported that FADD serves as an adaptor protein which recruits the Ced-3-related protease, MACHα/FLICE (caspase 8), into the death signaling complex [Boldin et al., *Cell*, 85:803–815 (1996); Muzio et al., *Cell*, 85:817–827 (1996)]. MACHα/FLICE appears to be the trigger that sets off a cascade of apoptotic proteases, including the interleukin-1β converting enzyme (ICE) and CPP32/Yama, which may execute some critical aspects of the cell death program [Fraser and Evan, supra].

It was recently disclosed that programmed cell death involves the activity of members of a family of cysteine proteases related to the *C. elegans* cell death gene, ced-3, and to the mammalian IL-1-converting enzyme, ICE. The activity of the ICE and CPP32/Yama proteases can be inhibited by the product of the cowpox virus gene, crmA [Ray et al., *Cell*, 69:597–604 (1992); Tewari et al., *Cell*, 81:801–809 (1995)]. Recent studies show that CrmA can inhibit TNFR1—and CD95-induced cell death [Enari et al., *Nature*, 375:78–81 (1995); Tewari et al., *J. Biol. Chem.*, 270:3255–3260 (1995)].

As reviewed recently by Tewari et al., TNFR1, TNFR2 and CD40 modulate the expression of proinflammatory and costimulatory cytokines, cytokine receptors, and cell adhesion molecules through activation of the transcription factor, NF-KB [Tewari et al., *Curr. Op. Genet. Develop.*, 6:39–44 (1996)]. NF-κB is the prototype of a family of dimeric transcription factors whose subunits contain conserved Rel regions [Verma et al., *Genes Develop.*, 9:2723–2735 (1995); Baldwin, *Ann. Rev. Immunol.*, 14:649–683 (1996)]. In its latent form, NF-κB is complexed with members of the IκB inhibitor family; upon inactivation of the IκB in response to certain stimuli, released NF-κB translocates to the nucleus where it binds to specific DNA sequences and activates gene transcription.

For other recent reviews of such signaling pathways see, e.g., Ashkenazi et al., *Science*, 281:1305–1308 (1998) and Nagata, *Cell*, 88:355–365 (1997).

SUMMARY OF THE INVENTION

Applicants have identified cDNA clones that encode novel polypeptides having certain sequence identity to previously-described tumor necrosis factor receptor protein (s), wherein the polypeptides are designated in the present application as "DNA98853" polypeptide and "DNA101848" polypeptide.

In one embodiment, the invention provides an isolated nucleic acid molecule comprising DNA encoding a DNA98853 polypeptide. In certain aspects, the isolated nucleic acid comprises DNA encoding the DNA98853 having amino acid residues 1 to 299 or 1 to 136 of FIG. 2 (SEQ ID NO:3), or is complementary to such encoding nucleic acid sequences, and remains stably bound to it under at least moderate, and optionally, under high stringency conditions. The isolated nucleic acid sequence may comprise the cDNA insert of the vector deposited on Apr. 6, 1999 as ATCC 203906 which includes the nucleotide sequence encoding DNA98853 polypeptide.

In another embodiment, the invention provides a vector comprising DNA encoding a DNA98853 polypeptide. A host cell comprising such a vector is also provided. By way of example, the host cells may be CHO cells, *E. coli*, or yeast. A process for producing DNA98853 polypeptides is further provided and comprises culturing host cells under conditions suitable for expression of DNA98853 polypeptide and recovering DNA98853 polypeptide from the cell culture.

In another embodiment, the invention provides isolated DNA98853 polypeptide. In particular, the invention provides isolated native sequence DNA98853 polypeptide, which in one embodiment, includes an amino acid sequence comprising residues 1 to 299 of FIG. 2 (SEQ ID NO:3). Additional embodiments of the present invention are directed to isolated extracellular domain sequences of a DNA98853 polypeptide comprising amino acids 1 to 136 of the amino acid sequence shown in FIG. 2 (SEQ ID NO:3), or fragments thereof. Optionally, the DNA98853 polypeptide is obtained or is obtainable by expressing the polypeptide encoded by the cDNA insert of the vector deposited on Apr. 6, 1999 as ATCC 203906.

In another embodiment, the invention provides chimeric molecules comprising a DNA98853 polypeptide or extracellular domain sequence or other fragment thereof fused to a heterologous polypeptide or amino acid sequence. An example of such a chimeric molecule comprises a DNA98853 polypeptide fused to an epitope tag sequence or a Fc region of an immunoglobulin.

In another embodiment, the invention provides an antibody which specifically binds to a DNA98853 polypeptide or extracellular domain thereof. Optionally, the antibody is a monoclonal antibody.

In a still further embodiment, the invention provides diagnostic and therapeutic methods using the DNA98853 polypeptide or DNA encoding the DNA98853 polypeptide.

In one embodiment, the invention provides an isolated nucleic acid molecule comprising DNA encoding a DNA101848 polypeptide. In certain aspects, the isolated nucleic acid comprises DNA encoding the DNA101848 polypeptide having amino acid residues 1 to 297 or 1 to 136 of FIG. 4 (SEQ ID NO:6), or is complementary to such encoding nucleic acid sequences, and remains stably bound to it under at least moderate, and optionally, under high stringency conditions. The isolated nucleic acid sequence may comprise the cDNA insert of the vector deposited on Apr. 6, 1999 as ATCC 203907 which includes the nucleotide sequence encoding DNA101848 polypeptide.

In another embodiment, the invention provides a vector comprising DNA encoding a DNA101848 polypeptide. A host cell comprising such a vector is also provided. By way of example, the host cells may be CHO cells, E. coli, or yeast. A process for producing DNA101848 polypeptides is further provided and comprises culturing host cells under conditions suitable for expression of DNA101848 polypeptide and recovering DNA101848 polypeptide from the cell culture.

In another embodiment, the invention provides isolated DNA101848 polypeptide. In particular, the invention provides isolated native sequence DNA101848 polypeptide, which in one embodiment, includes an amino acid sequence comprising residues 1 to 297 of FIG. 4 (SEQ ID NO:6). Additional embodiments of the present invention are directed to isolated extracellular domain sequences of a DNA101848 polypeptide comprising amino acids 1 to 136 of the amino acid sequence shown in FIG. 4 (SEQ ID NO:6), or fragments thereof. Optionally, the DNA101848 polypeptide is obtained or is obtainable by expressing the polypeptide encoded by the cDNA insert of the vector deposited on Apr. 6, 1999 as ATCC 203907.

In another embodiment, the invention provides chimeric molecules comprising a DNA101848 polypeptide or extracellular domain sequence or other fragment thereof fused to a heterologous polypeptide or amino acid sequence. An example of such a chimeric molecule comprises a DNA101848 polypeptide fused to an epitope tag sequence or a Fc region of an immunoglobulin.

In another embodiment, the invention provides an antibody which specifically binds to a DNA101848 polypeptide or extracellular domain thereof. Optionally, the antibody is a monoclonal antibody.

In a still further embodiment, the invention provides diagnostic and therapeutic methods using the DNA101848 polypeptide or DNA encoding the DNA101848 polypeptide.

Applicants have surprisingly found that the TNF family ligand referred to as EDA-A2 binds to the DNA101848 receptor. The present invention thus provides for novel methods of using antagonists or agonists of these TNF-related ligand and receptors. The antagonists and agonists described herein find utility for, among other things, in vitro, in situ, or in vivo diagnosis or treatment of mammalian cells or pathological conditions associated with the presence (or absence) of EDA-A2.

The methods of use include methods to treat pathological conditions or diseases in mammals associated with or resulting from increased or enhanced EDA-A2 expression and/or activity. In the methods of treatment, EDA-A2 antagonists may be administered to the mammal suffering from such pathological condition or disease. The EDA-A2 antagonists contemplated for use in the invention include DNA101848 or DNA98853 receptor immunoadhesins, as well as antibodies against the DNA101848 or DNA98853 receptor, which preferably block or reduce the respective receptor binding or activation by EDA-A2. The EDA-A2 antagonists contemplated or use further include anti-EDA-A2 antibodies which are capable of blocking or reducing binding of the ligand to the DNA101848 or DNA98853 receptors. Still further antagonist molecules include covalently modified forms, or fusion proteins, comprising DNA101848 or DNA98853. By way of example, such antagonists may include pegylated DNA101848 or DNA98853 or DNA101848 or DNA98853 fused to heterologous sequences such as epitope tags or leucine zippers.

In another embodiment of the invention, there are provided methods for the use of EDA-A2 antagonists to block or neutralize the interaction between EDA-A2 and DNA101848 or DNA98853. For example, the invention provides a method comprising exposing a mammalian cell to one or more EDA-A2 antagonists in an amount effective to decrease, neutralize or block activity of the EDA-A2 ligand. The cell may be in cell culture or in a mammal, e.g. a mammal suffering from, for instance, an immune related disease or cancer. Thus, the invention includes a method for treating a mammal suffering from a pathological condition such as an immune related disease or cancer comprising administering an effective amount of one or more EDA-A2 antagonists, as disclosed herein.

The invention also provides compositions which comprise one or more EDA-A2 antagonists. Optionally, the compositions of the invention will include pharmaceutically acceptable carriers or diluents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a nucleotide sequence (SEQ ID NO: 1) (and complementary sequence (SEQ ID NO:2)) of a native sequence DNA98853 polypeptide cDNA (nucleotides 1–903). Also presented is the position of three cysteine-rich repeats encoded by nucleotides 10–126, 133–252 and 259–357 as underlined. The putative transmembrane domain of the protein is encoded by nucleotides 409–474 in the figure.

FIG. 2 shows the amino acid sequence (SEQ ID NO:3) derived from nucleotides 1–900 of the nucleotide 1) sequence shown in FIG. 1. A potential transmembrane domain exists between and including amino acids 137 to 158 in the figure.

FIG. 3 shows a nucleotide sequence (SEQ ID NO:4) (and complementary sequence (SEQ ID NO:5)) of a native sequence DNA101848 polypeptide cDNA (nucleotides 1–897). Also presented is the position of three cysteine-rich repeats encoded by nucleotides 10–126, 133–252 and 259–357 as underlined. The putative transmembrane domain of the protein is encoded by nucleotides 409–474 in the figure.

FIG. 4 shows the amino acid sequence (SEQ ID NO:6) derived from nucleotides 1–894 of the nucleotide sequence shown in FIG. 3. A potential transmembrane domain exists between and including amino acids 137 to 158 in the figure.

FIG. 5 illustrates an alignment of the amino acid sequence of a DNA101848 polypeptide (SEQ ID NO:6) with the amino acid sequence of a DNA98853 polypeptide (SEQ ID NO:3). The alignment shows sequence identity except for a two amino acid gap in the DNA101848 polypeptide.

FIG. 6 illustrates a schematic representation of a novel inverse long distance PCR procedure carried out to isolate the full length coding sequence for DNA98853 and DNA101848 polypeptides.

FIG. 7 illustrates Northern Blots showing expression levels of DNA101848 polypeptide in several human cell lines and tissues.

FIGS. 8A–C illustrate the results of assays of DNA101848 polypeptide to determine NF-KB activation. These assays analyze expression of a reporter gene driven by a promoter containing a NF-KB responsive element from the E-selectin gene.

FIG. 9 shows the nucleotide sequence of Incyte clone 509 1511H. (SEQ ID No:7)

FIGS. 10A–10D show the results of an immunostaining assay of MCF-7 (transfected cells with N-terminal or C-terminal DNA101848 Flag constructs) to determine the transmembrane properties of the DNA101848 receptor.

FIG. 11 shows the results of an immunostaining assay of COS7 transfected cells (with various TNF-related ligands) to determine whether DNA101848 is a receptor for EDA-A2.

FIGS. 12A–12D show the results of an in situ assay of COS7 cells (transfected with DNA101848 or empty vector). The results showed that AP-EDA-A2, but not AP-TNF-alpha or AP-TALL-1, bound to the cells transfected with DNA101848.

FIG. 13 shows the results of a Western blot assay to determine whether Flag tagged forms of EDA-A2 specifically bind to DNA101848.

FIGS. 14A–14B illustrate the results of assays of DNA101848 and EDA-A2 to determine NF-KB activation.

FIGS. 15A–15B illustrate the results of Western blot assays showing the effects of DNA101848 and EDA-A2 on NF-KB activation.

DETAILED DESCRIPTION OF THE PREFERRED EMBODIMENTS

I. Definitions

The term "DNA98853 polypeptide" when used herein encompasses native sequence DNA98853 polypeptide and DNA98853 polypeptide variants (which are further defined herein). The DNA98853 polypeptides may be isolated from a variety of sources, such as from human tissue types or from another source, or prepared by recombinant or synthetic methods.

A "native sequence DNA98853 polypeptide" comprises a polypeptide having the same amino acid sequence as a DNA98853 polypeptide derived from nature. Such native sequence DNA98853 polypeptide can be isolated from nature or can be produced by recombinant or synthetic means. The term "native sequence DNA98853 polypeptide" specifically encompasses naturally-occurring truncated or secreted forms of a DNA98853 polypeptide (e.g., soluble forms containing for instance, an extracellular domain sequence), naturally-occurring variant forms (e.g., alternatively spliced forms) and naturally-occurring allelic variants of a DNA98853 polypeptide. In one embodiment of the invention, the native sequence DNA98853 polypeptide is a mature or full-length native sequence DNA98853 polypeptide comprising amino acids 1 to 299 of FIG. 2 (SEQ ID NO:3). In another embodiment of the invention, the native sequence DNA98853 polypeptide is an extracellular domain sequence of the full-length DNA98853 polypeptide protein, wherein the putative transmembrane domain of the full-length DNA98853 polypeptide protein includes amino acids 137–158 of the sequence shown in FIG. 2 (SEQ ID NO:3). Thus, additional embodiments of the present invention are directed to polypeptides comprising amino acids 1–136 of the amino acid sequence shown in FIG. 2 (SEQ ID NO:3). Optionally, the DNA98853 polypeptide is obtained or obtainable by expressing the polypeptide encoded by the cDNA insert of the vector DNA98853 deposited on Apr. 6, 1999 as ATCC 203906.

The "DNA98853 polypeptide extra cellular domain" or "DNA98853 polypeptide ECD" refers to a form of the DNA98853 which is essentially free of the transmembrane and cytoplasmic domains of the DNA98853 polypeptide. Ordinarily, DNA98853 polypeptide ECD will have less than 1% of such transmembrane and/or cytoplasmic domains and preferably, will have less than 0.5% of such domains. Optionally, DNA98853 polypeptide ECD will comprise amino acid residues 1–136 of FIG. 2 (SEQ ID NO:3). Included are deletion variants or fragments of the full length or ECD in which one or more amino acids are deleted from the N- or C-terminus. Preferably, such deletion variants or fragments possess a desired activity, such as described herein. It will be understood that any transmembrane domain identified for the DNA98853 polypeptide of the present invention is identified pursuant to criteria routinely employed in the art for identifying that type of hydrophobic domain. The exact boundaries of a transmembrane domain may vary but most likely by no more than about 5 amino acids at either end of the domain as initially identified. Accordingly, the DNA98853 polypeptide ECD may optionally comprise amino acids 1 to X of FIG. 2 (SEQ ID NO:3), wherein X is any one of amino acid residues 131 to 141 of FIG. 2 (SEQ ID NO:3).

"DNA98853 polypeptide variant" means a DNA98853 polypeptide as defined below having at least about 80% amino acid sequence identity with the DNA98853 polypeptide having the deduced amino acid sequence shown in FIG. 2 (SEQ ID NO:3) for a full-length native sequence DNA98853 polypeptide or a DNA98853 polypeptide ECD sequence. Such DNA98853 polypeptide variants include, for instance, DNA98853 polypeptide wherein one or more amino acid residues are added, or deleted, at the N- or C-terminus of the sequence of FIG. 2 (SEQ ID NO:3). Ordinarily, a DNA98853 polypeptide variant will have at least about 80% amino acid sequence identity, preferably at least about 85% amino acid sequence identity, more preferably at least about 90% amino acid sequence identity, even more preferably at least about 95% amino acid sequence identity and yet more preferably 98% amino acid sequence identity with the amino acid sequence of FIG. 2 (SEQ ID NO:3).

The term "DNA101848 polypeptide" when used herein encompasses native sequence DNA101848 polypeptide and DNA101848 polypeptide variants (which are further defined herein). The DNA101848 polypeptides may be isolated from a variety of sources, such as from human tissue types or from another source, or prepared by recombinant or synthetic methods.

A "native sequence DNA101848 polypeptide" comprises a polypeptide having the same amino acid sequence as a DNA101848 polypeptide derived from nature. Such native sequence DNA101848 polypeptide can be isolated from nature or can be produced by recombinant or synthetic means. The term "native sequence DNA101848 polypeptide" specifically encompasses naturally-occurring truncated or secreted forms of a DNA101848 polypeptide (e.g., soluble forms containing for instance, an extracellular domain sequence), naturally-occurring variant forms (e.g., alternatively spliced forms) and naturally-occurring allelic variants of a DNA101848 polypeptide. In one embodiment of the invention, the native sequence DNA101848 polypeptide is a mature or full-length native sequence DNA101848 polypeptide comprising amino acids 1 to 297 of FIG. 4 (SEQ ID NO:6). In yet another embodiment of the invention, the native sequence DNA101848 polypeptide is an extracellular domain sequence of the full-length DNA101848 polypeptide protein, wherein the putative transmembrane domain of the full-length DNA101848 polypeptide protein includes amino acids 137–158 of the sequence shown in FIG. 4 (SEQ ID NO:6). Thus, additional embodiments of the present invention are directed to polypeptides comprising amino acids 1–136 of the amino acid sequence shown in FIG. 4 (SEQ ID NO:6). Optionally, the DNA101848 polypeptide is obtained or obtainable by expressing the polypeptide encoded by the cDNA insert of the vector DNA101848 deposited on Apr. 6, 1999 as ATCC 203907.

The "DNA101848 polypeptide extracellular domain" or "DNA101848 polypeptide ECD" refers to a form of the DNA101848 polypeptide which is essentially free of the transmembrane and cytoplasmic domains of the DNA101848 polypeptide. Ordinarily, DNA101848 polypeptide ECD will have less than 1% of such transmembrane and/or cytoplasmic domains and preferably, will have less than 0.5% of such domains. Optionally, DNA101848 polypeptide ECD will comprise amino acid residues 1–136 of FIG. 4 (SEQ ID NO:6). Included are deletion variants or fragments of the full length or ECD in which one or more amino acids are deleted from the N- or C-terminus. Preferably, such deletion variants or fragments possess a desired activity, such as described herein. It will be understood that any transmembrane domain identified for the DNA101848 polypeptide of the present invention is identified pursuant to criteria routinely employed in the art for identifying that type of hydrophobic domain. The exact boundaries of a transmembrane domain may vary but most likely by no more than about 5 amino acids at either end of the domain as initially identified. Accordingly, the DNA101848 polypeptide ECD may optionally comprise amino acids 1 to X of FIG. 4 (SEQ ID NO:6), wherein X is any one of amino acid residues 131 to 141 of FIG. 4 (SEQ ID NO:6).

"DNA101848 polypeptide variant" means a DNA101848 polypeptide as defined below having at least about 80% amino acid sequence identity with the DNA101848 polypeptide having the deduced amino acid sequence shown in FIG. 4 (SEQ ID NO:6) for a full-length native sequence DNA101848 polypeptide or a DNA101848 polypeptide ECD sequence. Such DNA101848 polypeptide variants include, for instance, DNA101848 polypeptides wherein one or more amino acid residues are added, or deleted, at the N- or C-terminus of the sequence of FIG. 4 (SEQ ID NO:6). Ordinarily, a DNA101848 polypeptide variant will have at least about 80% amino acid sequence identity, preferably at least about 85% amino acid sequence identity, more preferably at least about 90% amino acid sequence identity, even more preferably at least about 95% amino acid sequence identity and yet more preferably 98% amino acid sequence identity with the amino acid sequence of FIG. 4 (SEQ ID NO:6).

"Percent (%) amino acid sequence identity" with respect to the polypeptide amino acid sequences identified herein is defined as the percentage of amino acid residues in a candidate sequence that are identical with the amino acid residues in, e.g., a DNA98853 polypeptide or DNA101848 polypeptide sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, may be performed without undue experimentation, and calculations of identity values may be obtained with definiteness. Alignment for purposes of determining percent amino acid sequence identity can be achieved in various ways that are within the skill in the art, for instance, using available computer software such as ALIGN or Megalign (DNASTAR) software, WU-BLAST-2 [Altschul et al., Meth. Enzym., 266:460–480 (1996)], and ALIGN-2 [authored by Genentech, Inc., and filed with the U.S. Copyright Office on Dec. 10, 1991]. Those skilled in the art can determine appropriate parameters for measuring alignment, including any algorithms needed to achieve maximal alignment over the full length of the sequences being compared. One may optionally perform the alignment using set default parameters in the computer software program.

The term "epitope tagged" where used herein refers to a chimeric polypeptide comprising a DNA98853 polypeptide, or a DNA101848 polypeptide, or a domain sequence thereof, fused to a "tag polypeptide". The tag polypeptide has enough residues to provide an epitope against which an antibody may be made, or which can be identified by some other agent, yet is short enough such that it does not interfere with the activity of the DNA98853 polypeptide or DNA101848 polypeptide. The tag polypeptide preferably is also fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the DNA98853 polypeptide or DNA101848 polypeptide natural environment will not be present. Ordinarily, however, isolated polypeptide will be prepared by at least one purification step.

An "isolated" DNA98853 polypeptide-encoding nucleic acid molecule is a nucleic acid molecule that is identified and separated from at least one contaminant nucleic acid molecule with which it is ordinarily associated in the natural source of the DNA98853 polypeptide polypeptide-encoding nucleic acid. An isolated DNA98853 polypeptide-encoding nucleic acid molecule is other than in the form or setting in which it is found in nature. Isolated DNA98853 polypeptide-encoding nucleic acid molecules therefore are distinguished from the DNA98853 polypeptide-encoding nucleic acid molecule as it exists in natural cells. However, an isolated DNA98853 polypeptide-encoding nucleic acid molecule includes DNA98853 polypeptide-encoding nucleic acid molecules contained in cells that ordinarily express DNA98853 polypeptide where, for example, the nucleic acid molecule is in a chromosomal location different from that of natural cells.

An "isolated" DNA101848 polypeptide-encoding nucleic acid molecule is a nucleic acid molecule that is identified and separated from at least one contaminant nucleic acid molecule with which it is ordinarily associated in the natural source of the DNA101848 polypeptide-encoding nucleic acid. An isolated DNA101848 polypeptide-encoding nucleic acid molecule is other than in the form or setting in which it is found in nature. Isolated DNA101848 polypeptide-encoding nucleic acid molecules therefore are distinguished from the DNA101848 polypeptide-encoding nucleic acid molecule as it exists in natural cells. However, an isolated DNA101848 polypeptide-encoding nucleic acid molecule includes DNA101848 polypeptide-encoding nucleic acid molecules contained in cells that ordinarily express DNA101848 polypeptide where, for example, the nucleic acid molecule is in a chromosomal location different from that of natural cells.

"EDA-A2" or "EDA-A2 ligand" refer to the TNF-related molecule described, e.g, by Bayes et al., *Human Molecular Genetics*, 7:1661–1669 (1998). The terms "EDA-A2" or "EDA-A2 polypeptide" when used herein encompass "native sequence EDA-A2 polypeptides" and "EDA-A2 variants". "EDA-A2" is a designation given to those polypeptides which are encoded by the nucleic acid molecules comprising the polynucleotide sequence shown in Bayes et al., supra and variants thereof, nucleic acid molecules comprising the sequence, and variants thereof as well as fragments of the above which have the biological activity (preferably, the ability to bind DNA101848 or DNA98835 receptors) of the native sequence EDA-A2 disclosed in Bayes et al., sunra. Biologically active variants of EDA-A2 will preferably have at least 80%, more preferably, at least 90%, and even more preferably, at least 95% amino acid sequence identity with the native sequence EDA-A2 polypeptide described by Bayes et al., supra. A "native sequence" EDA-A2 polypeptide comprises a polypeptide having the same amino acid sequence as the corresponding EDA-A2 polypeptide derived from nature. Such native sequence EDA-A2 polypeptides can be isolated from nature or can be produced by recombinant and/or synthetic means. The term "native sequence EDA-A2 polypeptide" specifically encompasses naturally-occurring truncated or secreted forms (e.g., an extracellular domain sequence), naturally-occurring variant forms (e.g., alternatively spliced forms) and naturally-occurring allelic variants of the polypeptide. Applicants did find that the EDA-A1 form of the ligand disclosed in Bayes et al., supra, did not bind Applicants' DNA101848-hFc construct (the construct is described in the Examples below), and therefore, it is believed that that particular EDA-A1 form of the ligand may not be a biologically active variant for purposes of this definition.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-DNA98853 polypeptide monoclonal antibodies (including agonist, antagonist, and neutralizing antibodies), single anti-DNA101848 polypeptide monoclonal antibodies (including agonist, antagonist, and neutralizing antibodies), anti-DNA98853 polypeptide antibody compositions with polyepitopic specificity, and anti-DNA101848 polypeptide antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of DNA98853 polypeptide which retain the biologic and/or immunologic activities of native or naturally-occurring DNA98853 polypeptide and to form(s) of DNA101848 polypeptide which retain the biologic and/or immunologic activities of native or naturally-occurring DNA101848 polypeptide. Such activities include, for instance, the ability to modulate (either in an agonistic or antagonistic manner) apoptosis, proinflammatory or autoimmune responses in mammalian cells, as well as the ability to bind EDA-A2 ligand. Agonistic activity will include the ability to stimulate or enhance an activity, while antagonistic activity will include the ability to block, suppress or neutralize an activity.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "antagonist" is used in the broadest sense, and includes any molecule that partially or fully blocks, inhibits, or neutralizes one or more biological activities of EDA-A2 polypeptide, in vitro, in situ, or in vivo. Examples of such biological activities of EDA-A2 include binding of DNA101848 or DNA98853, and activation of NF-KB, as well as those further reported in the literature.

The term "EDA-A2 antagonist" refers to any molecule that partially or fully blocks, inhibits, or neutralizes a biological activity of EDA-A2, and include, but are not limited to, soluble forms of DNA101848 or DNA98853 receptor such as an extracellular domain sequence of DNA101848 or DNA98853, DNA101848 or DNA98853 receptor inmmunoadhesins, DNA101848 or DNA98853 receptor fusion proteins, covalently modified forms of DNA101848 or DNA98853 receptor, DNA101848 or DNA98853 variants, and DNA101848 or DNA98853 receptor antibodies. To determine whether an EDA-A2 antagonist molecule partially or fully blocks, inhibits or neutralizes a biological activity of EDA-A2, assays may be conducted to assess the effect(s) of the antagonist molecule on, for example, binding of EDA-A2 to DNA101848 or DNA98853, or NF-KB activation by the respective ligand. Such assays may be conducted in known in vitro or in vivo assay formats, for instance, in transfected cells expressing DNA101848. Preferably, the EDA-A2 antagonist employed in the methods described herein will be capable of blocking or neutralizing at least one type of EDA-A2 activity, which may optionally be determined in assays such as described herein. Optionally, an EDA-A2 antagonist will be capable of reducing or inhibiting binding of EDA-A2 to DNA101848 or DNA98853 by at least 50%, preferably, by at least 90%, more preferably by at least 99%, and most preferably, by 100%, as compared to a negative control molecule, in a binding assay, such as described in the Examples.

The terms "treating", "treatment" and "therapy" as used herein refer to curative therapy, prophylactic therapy, and preventative therapy.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis, or DNA electrophoresis, all which are known in the art.

The terms "cancer", "cancerous", and "malignant" refer to or describe the physiological condition in mammals that is typically characterized by unregulated cell growth. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis, Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

"Autoimimune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, lupus erythematous, thyroiditis, rheumatoid arthritis, psoriasis, multiple sclerosis, autoimmune diabetes, and inflammatory bowel disease (IBD).

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of disease. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol, Bristol-Myers Squibb Oncology, Princeton, N.J.), and doxetaxel (Taxotere, Rhône-Poulenc Rorer, Antony, Rnace), toxotere, methotrexate, cisplatin, melphalan, CPT-11, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action such as tamoxifen and onapristone.

A "growth inhibitory agent" when used herein refers to a compound or composition which inhibits growth of a cell, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al (WB Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

The term "mammal" as used herein refers to any mammal classified as a mammal, including humans, cows, horses, dogs and cats. In a preferred embodiment of the invention, the mammal is a human.

II. Compositions and Methods of the Invention

A. Full-length DNA98853 Polypeptide

The present invention provides newly identified and isolated nucleotide sequences encoding polypeptides referred to in the present application as a DNA98853 polypeptide. In particular, Applicants have identified and isolated cDNA encoding a DNA98853 polypeptide, as disclosed in further detail in the Examples below. Using BLAST and FastA sequence alignment computer programs (with set default parameters), Applicants found that portions of the DNA98853 polypeptide have certain sequence identity with various members of the tumor necrosis factor receptor family. Accordingly, it is presently believed that DNA98853 polypeptide disclosed in the present application is a newly identified member of the tumor necrosis factor receptor family of polypeptides.

The activation of NF-KB by the DNA98853 polypeptide suggests a role for this protein in modulating apoptosis, proinflammatory and autoimmune responses in mammalian cells. It is contemplated for instance, that a DNA98853 polypeptide immunoadhesin molecule (e.g., a DNA98853 polypeptide ECD-Ig construct) could be used in an antagonistic manner to block NF-KB activation.

B. Full-length DNA 101848 Polypeptide

The present invention provides newly identified and isolated nucleotide sequences encoding polypeptides referred to in the present application as a DNA101848 polypeptide. In particular, Applicants have identified and isolated cDNA encoding a DNA101848 polypeptide, as disclosed in further detail in the Examples below. Using BLAST and FastA sequence alignment computer programs (with set default parameters), Applicants found that portions of the DNA101848 polypeptide have certain sequence identity with various members of the tumor necrosis factor receptor family. Accordingly, it is presently believed that DNA101848 polypeptide disclosed in the present application is a newly identified member of the tumor necrosis factor receptor family of polypeptides.

DNA101848 polypeptide mRNA expression was observed in several cells and tissues. As shown in FIG. 7, relatively high expression levels of DNA101848 polypeptide mRNA were detected in two tumor cell lines, lung carcinoma A549 and melanoma G361. Relatively weak expression levels were found in prostate, testis, ovary, thyroid, spinal cord and adrenal gland tissues. Interestingly, a smaller transcript with relatively high expression level existed in stomach tissue.

The activation of NF-KB by the DNA101848 polypeptide suggests a role for this protein in modulating apoptosis, proinflammatory and autoimmune responses in mammalian cells. It is contemplated for instance, that a DNA101848 polypeptide immunoadhesin molecule (e.g., a DNA101848 polypeptide ECD-Ig construct) could be used in an antagonistic manner to block NF-KB activation.

As described herein, Applicants have found that EDA-A2 acts as a ligand for DNA101848 receptor. Accordingly, various methods are described for use of EDA-A2 antagonists. Given the relatively high percentage of sequence identity between DNA101848 and DNA98853 receptors (particularly the complete (100%) sequence identity in their respective ECD regions), it is believed that various constructs of DNA98853 may be employed as EDA-A2 antagonists similarly to the antagonistic DNA101848 constructs described herein.

C. Variants of the DNA98853 and DNA101848 Polypeptides

In addition to the full-length native sequence DNA98853 polypeptide described herein, it is contemplated that DNA98853 polypeptide variants can be prepared. DNA98853 polypeptide variants can be prepared by introducing appropriate nucleotide changes into the DNA98853 polypeptide-encoding DNA, or by synthesis of the desired DNA98853 polypeptide. Those skilled in the art will appreciate that amino acid changes may alter post-translational processes of the DNA98853 polypeptide, such as changing the number or position of glycosylation sites or altering the membrane anchoring characteristics.

Variations in the native full-length sequence DNA98853 polypeptide or in various domains of the DNA98853 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the DNA98853 polypeptide that results in a change in the amino acid sequence of the DNA98853 polypeptide as compared with the native sequence DNA98853 polypeptide.

Optionally, the variation is by substitution of at least one amino acid with any other amino acid in one or more of the domains of the DNA98853 polypeptide.

Similarly, DNA101848 polypeptide variants can be prepared. DNA101848 polypeptide variants can be prepared by introducing appropriate nucleotide changes into the DNA101848 polypeptide-encoding DNA, or by synthesis of the desired DNA101848 polypeptide. Those skilled in the art will appreciate that amino acid changes may alter post-translational processes of the DNA101848 polypeptide, such as changing the number or position of glycosylation sites or altering the membrane anchoring characteristics.

Variations in the native full-length sequence DNA101848 polypeptide or in various domains of the DNA101848 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the DNA101848 polypeptide that results in a change in the amino acid sequence of the DNA101848 polypeptide as compared with the native sequence DNA101848 polypeptide. Optionally, the variation is by substitution of at least one amino acid with any other amino acid in one or more of the domains of the DNA101848 polypeptide.

Guidance in determining which amino acid residue may be inserted, substituted or deleted without adversely affecting the desired activity may be found by comparing the sequence of the polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in any of the in vitro assays described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., Gene, 34:3 (1985)], restriction selection mutagenesis [Wells et al., *Philos. Trans. R. Soc. London SerA*, 317:415 (1986)] or other known techniques can be performed on the cloned DNA to produce the DNA98853 polypeptide or DNA101848 polypeptide-encoding variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.*, 150:1 (1976)]. If alanine substitution does not yield adequate amounts of variant, an isosteric amino acid can be used.

D. Modifications of the DNA98853 or DNA101848 Polypeptides

Covalent modifications of DNA98853 polypeptides or of DNA101848 polypeptides are included within the scope of this invention. One type of covalent modification includes reacting targeted amino acid residues of a DNA98853 polypeptide with an organic derivatizing agent that is capable of reacting with selected side chains or the N- or C-terminal residues of a DNA98853 polypeptide. A DNA101848 polypeptide can be similarly modified at targeted amino acid residues having selected side chains or at its N- or C-terminal residues.

Derivatization with bifunctional agents is useful, for instance, for crosslinking DNA98853 polypeptide to a water-insoluble support matrix or surface for use in the method for purifying anti-DNA98853 polypeptide antibodies, and vice-versa. Such bifunctional agents are also useful for crosslinking DNA101848 polypeptide to a water-insoluble support matrix or surface for use in the method for purifying anti-DNA101848 polypeptide antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimnides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the DNA98853 polypeptide or DNA101848 polypeptide included within the scope of this invention comprises altering the native glycosylation pattern of either polypeptide. "Altering the native glycosylation pattern" is intended for purposes herein to mean deleting one or more carbohydrate moieties found in native sequence DNA98853 polypeptide, deleting one or more carbohydrate moieties found in native sequence DNA101848 polypeptide, adding one or more glycosylation sites that are not present in the native sequence DNA98853 polypeptide, and/or adding one or more glycosylation sites that are not present in the native sequence DNA101848 polypeptide.

Addition of glycosylation sites to DNA98853 polypeptides or DNA101848 polypeptides may be accomplished by altering the amino acid sequence thereof. The alteration may be made, for example, by the addition of, or substitution by, one or more serine or threonine residues to the native sequence DNA98853 polypeptide, or one or more serine or threonine residues to the native sequence DNA101848 polypeptide (for O-linked glycosylation sites). The DNA98853 polypeptide amino acid sequence may optionally be altered through changes at the DNA level, particularly by mutating the DNA encoding the DNA98853 polypeptide at preselected bases such that codons are generated that will translate into the desired amino acids. Similarly, the DNA101848 polypeptide amino acid sequence may optionally be altered through changes at the DNA level, particularly by mutating the DNA encoding the DNA101848 polypeptide at preselected bases such that codons are generated that will translate into the desired amino acids.

Another means of increasing the number of carbohydrate moieties on the DNA98853 polypeptide or DNA101848 polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the DNA98853 polypeptide or DNA101848 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of DNA98853 polypeptide or DNA101848 polypeptide comprises linking the polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

DNA98853 polypeptides of the present invention may also be modified in a way to form chimeric molecules comprising a DNA98853 polypeptide fused to another, heterologous polypeptide or amino acid sequence. In one embodiment, such a chimeric molecule comprises a fusion of a DNA98853 polypeptide with a tag polypeptide which provides an epitope to which an anti-tag antibody can selectively bind. The epitope tag is generally placed at the amino- or carboxyl-terminus of the DNA98853 polypeptide. The presence of such epitope-tagged forms of a DNA98853 polypeptide can be detected using an antibody against the tag polypeptide. Also, provision of the epitope tag enables the DNA98853 polypeptide to be readily purified by affinity purification using an anti-tag antibody or another type of affinity matrix that binds to the epitope tag. In an alternative embodiment, the chimeric molecule may comprise a fusion of a DNA98853 polypeptide with an immunoglobulin or a particular region of an immunoglobulin. For a bivalent form of the chimeric molecule, such a fusion could be to the Fc region of an IgG molecule. Optionally, the chimeric molecule will comprise a DNA98853 polypeptide ECD sequence fused to an Fc region of an IgG molecule.

Immunoadhesin molecules are further contemplated for use in the methods herein. The receptor immunoadhesins may comprise various forms of DNA101848 or DNA98853, such as the full length polypeptide as well as soluble forms of the receptor which comprise an extracellular domain (ECD) sequence or a fragment of the ECD sequence. In one embodiment, the molecule may comprise a fusion of the DNA101848 or DNA98853 receptor with an immunoglobulin or a particular region of an immunoglobulin. For a bivalent form of the immunoadhesin, such a fusion could be to the Fc region of an IgG molecule. The Ig fusions preferably include the substitution of a soluble (transmembrane domain deleted or inactivated) form of the receptor polypeptide in place of at least one variable region within an Ig molecule. In a particularly preferred embodiment, the immunoglobulin fusion includes the hinge, CH2 and CH3, or the hinge, CH1, CH2 and CH3 regions of an IgGI molecule. For the production of immunoglobulin fusions, see also U.S. Pat. No. 5,428,130 issued June 27, 1995 and Chamow et al., *TIBTECH*, 14:52–60 (1996).

The simplest and most straightforward immunoadhesin design combines the binding domain(s) of the adhesin (e.g. the extracellular domain (ECD) of a receptor) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc region of nmmunoglobulin G1 (IgG1,). It is possible to fuse the entire heavy chain constant region to the adhesin sequence. However, more preferably, a sequence beginning in the hinge region just upstream of the papain cleavage site which defines IgG Fc chemically (ie. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;

(b) $AC_H$-($AC_H$, $AC_L$-$AC_H$, $AC_L$-$V_HC_H$, or $V_LC_L$-$AC_H$);

(c) $AC_L$-$AC_H$-($AC_L$-$AC_H$, $AC_L$-$V_HC_H$, $V_LC_L$-$AC_H$, or $V_LC_L$-$V_HC_H$)

(d) $AC_L$-$V_HC_H$-($AC_H$, or $AC_L$-$V_HC_H$, or $V_LC_L$-$AC_H$);

(e) $V_LC_L$-$AC_H$-($AC_L$-$V_HC_H$, or $V_LC_L$-$AC_H$); and (f) $(A-Y)_n$-$(V_LC_L$-$V_HC_H)_2$, wherein each A represents identical or different adhesin amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the inumunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom et al., Mol. Immunol., 28:1027–1037 (1991).

Although the presence of an immunoglobulin light chain is not required in the immunoadhesins of the present invention, an immunoglobulin light chain might be present either covalently associated to an adhesin-immnunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., Cell, 61:1303–1313 (1990); and Stamenkovic et al., Cell, 66:1133–1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

DNA101848 polypeptides of the present invention may also be modified in a way to form chimeric molecules comprising a DNA101848 polypeptide fused to another, heterologous polypeptide or amino acid sequence. In one embodiment, such a chimeric molecule comprises a fusion of a DNA101848 polypeptide with a tag polypeptide which provides an epitope to which an anti-tag antibody can selectively bind. The epitope tag is generally placed at the amino- or carboxyl-terminus of the DNA101848 polypeptide. The presence of such epitope-tagged forms of a DNA101848 polypeptide can be detected using an antibody against the tag polypeptide. Also, provision of the epitope tag enables the DNA101848 polypeptide to be readily purified by affinity purification using an anti-tag antibody or another type of affinity matrix that binds to the epitope tag. In an alternative embodiment, the chimeric molecule may comprise a fusion of a DNA101848 polypeptide with an immunoglobulin or a particular region of an immunoglobulin. For a bivalent form of the chimeric molecule, such a fusion could be to the Fc region of an IgG molecule. Optionally, the chimeric molecule will comprise a DNA101848 polypeptide ECD sequence fused to an Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; an α-tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

The DNA98853 polypeptide of the present invention may also be modified in a way to form a chimeric molecule comprising a DNA98853 polypeptide fused to a leucine zipper. Similarly, the DNA101848 polypeptide of the present invention may also be modified in a way to form a chimeric molecule comprising a DNA101848 polypeptide fused to a leucine zipper. Various leucine zipper polypeptides have been described in the art. See, e.g., Landschulz et al., Science 240:1759 (1988); WO 94/10308; Hoppe et al., FEBS Letters 344:1991 (1994); Maniatis et al., Nature 341:24 (1989). It is believed that use of a leucine zipper fused to a DNA98853 polypeptide may be desirable to assist in dimerizing or trimerizing soluble DNA98853 polypeptide in solution, and that a leucine zipper fused to a DNA101848 polypeptide may be desirable to assist in dimerizing or trimerizing soluble DNA101848 polypeptide in solution. Those skilled in the art will appreciate that the leucine zipper may be fused at either the N- or C-terminal end of the DNA98853 or DNA101848 polypeptide molecule.

D. Preparation of Polypeptides

1. Preparation of DNA98853 Polypeptide

The description below relates primarily to production of a polypeptide, such as DNA98853 polypeptide, by culturing cells transformed or transfected with a vector containing DNA98853 polypeptide encoding nucleic acid. It is, of course, contemplated that alternative methods, which are well known in the art, may be employed to prepare DNA98853 polypeptides. For instance, the DNA98853 polypeptide sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc., 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of DNA98853 polypeptides may be chemically synthesized separately and combined using chemical or enzymatic methods to produce a full-length DNA98853 polypeptide.

2. Preparation of DNA101848 Polypeptide

The description below also relates to production of DNA101848 polypeptide by culturing cells transformed or transfected with a vector containing DNA101848 polypeptide encoding nucleic acid. It is, of course, contemplated that alternative methods, which are well known in the art, may be employed to prepare DNA101848 polypeptides. For instance, the DNA101848 polypeptide sequence, or portions thereof, may be produced by direct peptide synthesis using solid-phase techniques, as described above. Various portions of DNA101848 polypeptides may be chemically synthesized separately and combined using chemical or enzymatic methods to produce a full-length DNA101848 polypeptide.

3. Isolation of DNA Encoding the DNA98853 or DNA101848 Polypeptides

DNA encoding a DNA98853 polypeptide may be obtained from a cDNA library prepared from tissue believed to possess the DNA98853 polypeptide mRNA and to express it at a detectable level. Accordingly, human DNA98853 polypeptide-encoding DNA can be conveniently obtained from a cDNA library prepared from human tissue, such as described in the Examples. The DNA98853 polypeptide-encoding gene may also be obtained from a genomic library or by oligonucleotide synthesis.

Similarly, DNA encoding a DNA101848 polypeptide may be obtained from a cDNA library prepared from tissue believed to possess the DNA101848 polypeptide mRNA and to express it at a detectable level. Accordingly, human DNA101848 polypeptide-encoding DNA can be conveniently obtained from a cDNA library prepared from human tissue, such as described in the Examples. The DNA101848 polypeptide-encoding gene may also be obtained from a genomic library or by oligonucleotide synthesis.

Libraries can be screened with probes (such as antibodies to a DNA98853 polypeptide, antibodies to a DNA101848 polypeptide, or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding DNA98853 polypeptide or the gene encoding DNA101848 polypeptide is to use PCR methodology [Sambrook et al., supra; Dieffenbach et al., *PCR Primer:A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

4. Selection and Transformation of Host Cells

Host cells are transfected or transformed with expression or cloning vectors described herein for DNA98853 polypeptide production. Alternatively, host cells are transfected or transformed with expression or cloning vectors described herein for DNA101848 polypeptide production. The host cells are cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Grain-positive organisms, for example, Enterobacteriaceae such as *E. coli*. Various *E. coli* strains are publicly available, such as E. coli K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for vectors encoding DNA98853 polypeptide or vectors encoding DNA101848 polypeptide. *Saccharomyces cerevisiae* is a commonly used lower eukaryotic host microorganism.

Suitable host cells for the expression of glycosylated DNA98853 polypeptide or of glycosylated DNA101848 polypeptide are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL5 1). The selection of the appropriate host cell is deemed to be within the skill in the art.

5. Selection and Use of a Replicable Vector

The nucleic acid (e.g., cDNA or genornic DNA) encoding the desired DNA98853 polypeptide or encoding the desired DNA101848 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired DNA98853 polypeptide or the desired DNA101848 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, it may be a part of the DNA98853 polypeptide-encoding DNA that is inserted into the vector, or it may be a part of the DNA101848 polypeptide-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the DNA98853 polypeptide-encoding nucleic acid or the DNA101848 polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4–1 [Jones, *Genetics*, 85:12 (1977)].

Expression and cloning vectors usually contain a promoter operably linked to the DNA98853 polypeptide-encoding nucleic acid sequence or to the DNA101848 polypeptide-encoding nucleic acid sequence. The promoter directs mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21–25 (1983)]. Promoters for use in bacterial systems also will contain a Shine-Dalgarno (S.D.) sequence operably linked to the DNA encoding the DNA98853 polypeptide or operably linked to the DNA encoding the DNA101848 polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzvme Reg.*, 7:149 (1968); Holland, *Biochemistrv*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

DNA98853 polypeptide or DNA101848 polypeptide transcription from vectors in mammalian host cells is controlled, for example, by promoters obtained from the genomes of viruses such as polyoma virus, fowlpox virus (UK 2,211,504 published Jul. 5 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription by higher eukaryotes of a DNA encoding a DNA98853 polypeptide or of a DNA encoding a DNA101848 polypeptide may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the DNA98853 polypeptide coding sequence, but is preferably located at a site 5' from the promoter. Similarly, the enhancer may be spliced into the vector at a position 5' or 3' to the DNA101848 polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding DNA98853 polypeptide or of the mRNA encoding DNA101848 polypeptide.

Still other methods, vectors, and host cells suitable for adaptation to the synthesis of DNA98853 polypeptides and/or DNA101848 polypeptides in recombinant vertebrate cell culture are described in Gething et al., *Nature*, 293:620–625 (1981); Mantei et al., *Nature*, 281:40–46 (1979); EP 117,060; and EP 117,058.

6. Detecting Gene AmIification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence DNA98853 polypeptide, against a native sequence DNA101848 polypeptide, against a synthetic peptide based on the DNA sequences provided herein, against an exogenous sequence fused to DNA98853 polypeptide-encoding DNA and encoding a specific antibody epitope, or against an exogenous sequence fused to DNA101848 polypeptide-encoding DNA and encoding a specific antibody epitope.

7. Polypeptide Purification

Forms of DNA98853 polypeptide or DNA101848 polypeptide may be recovered from culture medium or from host cell lysates. If membrane-bound, they can be released from the membrane using a suitable detergent solution (e.g. Triton-X 100) or by enzymatic cleavage. Cells employed in expression of DNA98853 polypeptides or DNA101848 polypeptides can be disrupted by various physical or chemical means, such as freeze-thaw cycling, sonication, mechanical disruption, or cell lysing agents.

It may be desired to purify DNA98853 polypeptide or DNA101848 polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the DNA98853 polypeptide or DNA11848 polypeptide. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular DNA98853 polypeptide or DNA101848 polypeptide produced.

E. Uses for DNA98853 Polypeptide or DNA101848 Polypeptide

Nucleotide sequences (or their complement) encoding DNA98853 polypeptides, and nucleotide sequences or their complements encoding DNA101848 polypeptides, have various applications in the art of molecular biology, including uses as hybridization probes, in chromosome and gene mapping and in the generation of anti-sense RNA and DNA. DNA98853 polypeptide-encoding nucleic acid will also be useful for the preparation of DNA98853 polypeptides by the recombinant techniques described herein. Similarly, DNA101848 polypeptide-encoding nucleic acid will also be useful for the preparation of DNA101848 polypeptides by the recombinant techniques described herein.

The full-length DNA98853 nucleotide sequence (SEQ ID NO: 1) or the full-length native sequence DNA98853 polypeptide (SEQ ID NO:3) sequence, or portions thereof, may be used as hybridization probes for a cDNA library to isolate the full-length DNA98853 polypeptide gene or to isolate still other genes (for instance, those encoding naturally-occurring variants of DNA98853 polypeptide or DNA98853 polypeptide from other species) which have a desired sequence identity to the DNA98853 polypeptide nucleotide sequence disclosed in FIG. 1 (SEQ ID NO: 1). Optionally, the length of the probes will be about 20 to about 50 bases. The hybridization probes may be derived from the DNA98853 nucleotide sequence of SEQ ID NO: 1 as shown in FIG. 1 or from genomic sequences including promoters, enhancer elements and introns of native sequence DNA98853 polypeptide-encoding DNA. By way of example, a screening method will comprise isolating the coding region of the DNA98853 polypeptide gene using the known DNA sequence to synthesize a selected probe of about 40 bases.

Similarly, the full-length DNA101848 nucleotide sequence (SEQ ID NO:4) or the full-length native sequence DNA101848 polypeptide (SEQ ID NO:6) sequence, or portions thereof, may be used as hybridization probes for a cDNA library to isolate the full-length DNA101848 polypeptide gene or to isolate still other genes (for instance, those encoding naturally-occurring variants of DNA101848 polypeptide or DNA101848 polypeptide from other species) which have a desired sequence identity to the DNA101848 polypeptide sequence disclosed in FIG. 4 (SEQ ID NO:6).

Optionally, the length of the probes will be about 20 to about 50 bases. The hybridization probes may be derived from the DNA101848 nucleotide sequence of SEQ ID NO:4 as shown in FIG. 3 or from genomic sequences including promoters, enhancer elements and introns of native sequence DNA101848 polypeptide-encoding DNA. By way of example, a screening method will comprise isolating the coding region of the DNA 101848 polypeptide gene using the known DNA sequence to synthesize a selected probe of about 40 bases.

Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the DNA98853 polypeptide gene of the present invention, or complementary to that of the DNA101848 polypeptide gene of the present invention, can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related DNA98853 polypeptide sequences or DNA101848 polypeptide sequences.

Nucleotide sequences encoding a DNA98853 polypeptide or a DNA101848 polypeptide can also be used to construct hybridization probes for mapping the gene which encodes that polypeptide, and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for DNA98853 polypeptide encode a protein which binds to another protein (example, where the DNA98853 polypeptide functions as a receptor), the DNA98853 polypeptide can be used in assays to identify the other proteins or molecules involved in the binding interaction. Similarly, when the coding sequences for DNA101848 polypeptide encode a protein which binds to another protein (example, where the DNA101848 polypeptide functions as a receptor), the DNA101848 polypeptide can be used in assays to identify the other proteins or molecules involved in the binding interaction.

By such methods, inhibitors of the receptor/ligand binding interaction can be identified. Proteins involved in such binding interactions can also be used to screen for peptide or small molecule inhibitors or agonists of the binding interaction. Also, the receptor DNA98853 polypeptide or the receptor DNA101848 polypeptide can be used to isolate other correlative ligand(s). Screening assays can be designed to find lead compounds that mimic the biological activity of a native DNA98853 polypeptide, a native DNA101848 polypeptide, a receptor for DNA98853 polypeptide, or a receptor for DNA101848 polypeptide. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, inmunoassays and cell based assays, which are well characterized in the art.

Nucleic acids which encode DNA98853 polypeptide, DNA101848 polypeptide, or any of their modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding DNA98853 polypeptide can be used to clone genomic DNA encoding DNA98853 polypeptide in accordance with established techniques and the genomic sequences used to generate transgenic animals that contain cells which express DNA encoding DNA98853 polypeptide. In another embodiment, cDNA encoding DNA101848 polypeptide can be used to clone genomic DNA encoding DNA101848 polypeptide in accordance with established techniques and the genomic sequences used to generate transgenic animals that contain cells which express DNA encoding DNA101848 polypeptide.

Methods for generating transgenic animals, particularly animals such as mice or rats, have become conventional in the art and are described, for example, in U.S. Pat. Nos. 4,736,866 and 4,870,009. Typically, particular cells would be targeted for DNA98853 polypeptide and/or DNA101848 polypeptide transgene incorporation with tissue-specific enhancers. Transgenic animals that include a copy of a transgene encoding DNA98853 polypeptide introduced into the germ line of the animal at an embryonic stage can be used to examine the effect of increased expression of DNA encoding DNA98853 polypeptide. Alternatively, transgenic animals that include a copy of a transgene encoding DNA101848 polypeptide introduced into the germ line of the animal at an embryonic stage can be used to examine the effect of increased expression of DNA encoding DNA101848 polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of DNA98853 polypeptide can be used to construct a DNA98853 polypeptide "knock out" animal which has a defective or altered gene encoding DNA98853 polypeptide as a result of homologous recombination between the endogenous gene encoding DNA98853 polypeptide and altered genomic DNA encoding DNA98853 polypeptide introduced into an embryonic cell of the animal. For example, cDNA encoding DNA98853 polypeptide can be used to clone genomic DNA encoding DNA98853 polypeptide in accordance with established techniques. A portion of the genomic DNA encoding DNA98853 polypeptide can be deleted or replaced with another gene, such as a gene encoding a selectable marker which can be used to monitor integration.

Similarly, non-human homologues of DNA101848 polypeptide can be used to construct a DNA101848 polypeptide "knock out" animal which has a defective or altered gene encoding DNA101848 polypeptide as a result of homologous recombination between the endogenous gene encoding DNA 101848 polypeptide and altered genomic DNA encoding DNA101848 polypeptide introduced into an embryonic cell of the animal. For example, cDNA encoding DNA101848 polypeptide can be used to clone genomic DNA encoding DNA101848 polypeptide in accordance with established techniques. A portion of the genomic DNA encoding DNA101848 polypeptide can be deleted or replaced with another gene, such as a gene encoding a selectable marker which can be used to monitor integration.

Typically, in constructing a "knock out animal", several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized for instance, for their ability to defend against certain pathological conditions and for their development of pathological conditions due to absence of the DNA98853 polypeptide or the DNA101848 polypeptide.

The DNA98853 polypeptide or the DNA101848 polypeptide herein may be employed in accordance with the present invention by expression of such polypeptides in vivo, which is often referred to as gene therapy.

There are two major approaches to getting the nucleic acid (optionally contained in a vector) into the patient's cells: in vivo and ex vivo. For in vivo delivery the nucleic acid is injected directly into the patient, usually at the sites where the polypeptide is required. For example, DNA98853 polypeptide-encoding nucleic acid will be injected at the site of synthesis of the DNA98853 polypeptide, if known, or the site where biological activity of DNA98853 polypeptide is needed. For example, DNA101848 polypeptide-encoding nucleic acid will be injected at the site of synthesis of the DNA101848 polypeptide, if known, or the site where biological activity of DNA101848 polypeptide is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187).

There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (preferably retroviral) particle with a cellular receptor, followed by introduction of the nucleic acids contained by the particle into the cell. A commonly used vector for ex vivo delivery of the gene is a retrovirus.

The currently preferred in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinson et al., *Cancer Investigation*, 14(1): 54–65 (1996)). The most preferred vectors for use in gene therapy are viruses, most preferably adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding DNA98853 polypeptide or of a gene encoding DNA101848 polypeptide, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the DNA98853 polypeptide or DNA101848 polypeptide from a host cell in which it is placed. Preferably the signal sequence for this purpose is a mammnalian signal sequence, most preferably the native signal sequence for DNA98853 polypeptide or for DNA101848 polypeptide. Optionally, the vector construct may also include a signal that directs polyadenylation, as well as one or more restriction sites and a translation termination sequence. By way of example, such vectors will typically include a 5'LTR, a tRNA binding site, a packaging signal, an origin of second-strand DNA synthesis, and a 3'LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.*, 262: 4429–4432 (1987); and Wagner et al., *Proc. Natl. Acad. Sci. USA*, 87: 3410–3414 (1990). For a review of the currently known gene marking and gene therapy protocols, see Anderson et al., *Science*, 256: 808–813 (1992). See also WO 93/25673 and the references cited therein.

Suitable gene therapy and methods for making retroviral particles and structural proteins can be found in, e.g., U.S. Pat. No. 5,681,746.

DNA98853 polypeptides or DNA101848 polypeptides of the present invention which possess biological activity, for example such as related to that of the known tumor necrosis factor receptors may be employed both in vivo for therapeutic purposes and in vitro.

Therapeutic compositions of the DNA98853 polypeptide or the DNA101848 polypeptide can be prepared by mixing the desired molecule having the appropriate degree of purity with optional pharmaceutically acceptable carriers, excipients, or stabilizers (*Remington's Pharmaceutical Sciences*, 16th edition, Oslo, A. ed. (1980)), in the form of lyophilized formulations or aqueous solutions. Acceptable carriers, excipients, or stabilizers are preferably nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The DNA98853 polypeptides or DNA101848 polypeptides will typically be formulated in such vehicles at a concentration of about 0.1 mg/ml to 100 mg/ml.

DNA98853 polypeptide or DNA101848 polypeptide to be used for in vivo administration should be sterile. This is readily accomplished by filtration through sterile filtration membranes, prior to or following lyophilization and reconstitution. DNA98853 polypeptide or DNA101848 polypeptide ordinarily will be stored in lyophilized form or in solution if administered systemically. If in lyophilized form, DNA98853 polypeptide or DNA101848 polypeptide is typically formulated in combination with other ingredients for reconstitution with an appropriate diluent at the time for use. An example of a liquid formulation of DNA98853 polypeptide or DNA101848 polypeptide is a sterile, clear, colorless unpreserved solution filled in a single-dose vial for subcutaneous injection.

Therapeutic DNA98853 polypeptide or DNA101848 polypeptide compositions generally are placed into a container having a sterile access port, for example, an intravenous solution bag or vial having a stopper pierceable by a hypodermic injection needle. The formulations are preferably administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956).

DNA98853 polypeptide or DNA101848 polypeptide can also be administered in the form of sustained-released preparations. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 (1981) and Langer, *Chem. Tech.*, 12: 98–105 (1982) or poly(vinylalcohol)), polylactides (U.S. Patent No. 3,773,919, EP 58,481), copolymers of L-glutamic acid and gamma ethyl-L-glutamate (Sidman et al., *Biopolvmers*, 22: 547–556 (1983)), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(−)-3-hydroxybutyric acid (EP 133,988).

The therapeutically effective dose of a DNA98853 polypeptide or a DNA101848 polypeptide (or antibody thereto) will, of course, vary depending on such factors as the intended therapy (e.g., for modulating apoptosis, autoimmune or proinflammatory responses), the pathological condition to be treated, the method of administration, the type of compound being used for treatment, any co-therapy involved, the patient's age, weight, general medical condition, medical history, etc., and its determination is well within the skill of a practicing physician. Accordingly, it will be necessary for the therapist to titer the dosage and modify the route of administration as required to obtain the maximal therapeutic effect.

With the above guidelines, the effective dose generally is within the range of from about 0.001 to about 1.0 mg/kg.

The route of administration of DNA98853 polypeptide or DNA101848 polypeptide is in accord with known methods, e.g., by injection or infusion by intravenous, intramuscular, intracerebral, intraperitoneal, intracerobrospinal, subcutaneous, intraocular, intraarticular, intrasynovial, intrathecal, oral, topical, or inhalation routes, or by sustained-release systems. The DNA98853 polypeptide or DNA101848 polypeptide also are suitably administered by intratumoral, peritumoral, intralesional, or perilesional routes, to exert local as well as systemic therapeutic effects.

The effectiveness of the DNA98853 polypeptide or DNA101848 polypeptide treating the disorder may be improved by administering the active agent serially or in combination with another agent that is effective for those purposes, either in the same composition or as separate compositions. Examples of such agents include cytotoxic, chemotherapeutic or growth-inhibitory agents, cytokines and radiological treatments (such as involving irradiation or administration of radiological substances).

The effective amounts of the therapeutic agents administered in combination with DNA98853 polypeptide or DNA101848 polypeptide will be at the physician's discretion. Dosage administration and adjustment is done to achieve maximal management of the conditions to be treated.

The various therapeutic methods and compositions referred to above may be similarly employed for use of the EDA-A2 antagonists described herein.

F. Anti-DNA98853 Polypeptide and/or Anti-DNA101848 Polypeptide Antibodies

The present invention further provides anti-DNA98853 polypeptide antibodies and anti-DNA101848 polypeptide antibodies. Exemplary antibodies include polyclonal, monoclonal, humanized, bispecific, and heteroconjugate antibodies.

1. Polyclonal Antibodies

The anti-DNA98853 polypeptide antibodies and anti-DNA101848 polypeptide antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. For anti-DNA98853 polypeptide antibodies, the immunizing agent may include the DNA98853 polypeptide or a fusion protein thereof. For anti-DNA101848 polypeptide antibodies, the immunizing agent may include the DNA101848 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-DNA98853 polypeptide antibodies or anti-DNA101848 polypeptide antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

For anti-DNA98853 polypeptide antibodies, the immunizing agent will typically include the DNA98853 polypeptide or a fusion protein thereof. For anti-DNA101848 polypeptide antibodies, the immunizing agent will typically include the DNA101848 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against a DNA98853 polypeptide or a DNA101848 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-inumunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-DNA98853 polypeptide antibodies and anti-DNA101848 polypeptide antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapv*, Alan R. Liss, p.77 (1985) and Boerner et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for a DNA98853 polypeptide or for a DNA101848 polypeptide, and the other one is for any other antigen, preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconiugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 20 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-DNA98853 Polypeptide Antibodies and for anti-DNA101848 Polypeptide Antibodies The anti-DNA98853 polypeptide antibodies and anti-DNA101848 polypeptide antibodies of the present invention have various utilities. The anti-DNA98853 polypeptide antibodies or anti-DNA101848 polypeptide 30 antibodies may be used in therapy, using techniques and methods of administration described above. Also, for example, anti-DNA98853 polypeptide antibodies and anti-DNA101848 polypeptide antibodies may be used in diagnostic assays for the corresponding polypeptides, e.g., detecting expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluores isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-DNA98853 polypeptide antibodies also are useful for the affinity purification of DNA98853 polypeptides from recombinant cell culture or natural sources. In this process, the antibodies against a DNA98853 polypeptide are immobilized on a suitable support, such a Sephadex resin or filter paper, using methods well known in the art. The immobilized antibody then is contacted with a sample containing the DNA98853 polypeptide to be purified, and thereafter the support is washed with a suitable solvent that will remove substantially all the material in the sample except the DNA98853 polypeptide, which is bound to the immobilized antibody. Finally, the support is washed with another suitable solvent that will release the DNA98853 polypeptide from the antibody.

Anti-DNA101848 polypeptide antibodies also are useful for the affinity purification of DNA101848 polypeptides from recombinant cell culture or natural sources. In this process, the antibodies against a DNA101848 polypeptide are immobilized on a suitable support, such a Sephadex resin or filter paper, using methods well known in the art. The immobilized antibody then is contacted with a sample containing the DNA101848 polypeptide to be purified, and thereafter the support is washed with a suitable solvent that will remove substantially all the material in the sample except the DNA101848 polypeptide, which is bound to the immobilized antibody. Finally, the support is washed with another suitable solvent that will release the DNA101848 polypeptide from the antibody.

H. Articles of Manufacture

An article of manufacture such as a kit containing DNA98853 polypeptide, DNA101848 polypeptide, or antibodies thereto useful for the diagnosis or treatment of the disorders described herein comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is the DNA98853 polypeptide, the DNA101848 polypeptide, or an antibody thereto. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Virginia.

Example 1

Isolation of cDNA Clones Encoding Human DNA98853 Polypeptide

Based upon the DNA sequence of Incyte clone 509 1511H (SEQ ID NO:7) shown in FIG. 9 (from the Incyte Pharmaceuticals LIFESEQ™ database), oligonucleotides were synthesized to identify by PCR a cDNA library that contained the sequence of interest. These oligonucleotides were:
Forward primer:
  5' GAGGGGGCTGGGTGAGATGTG 3' (509-1) (SEQ ID NO:8)
Reverse primer:
  5' TGCTTTTGTACCTGCGAGGAOG 3' (509-4AS) (SEQ ID NO:9)

To isolate the full length coding sequence for DNA98853 polypeptide, an inverse long distance PCR procedure was carried out (FIG. 6). The PCR primers generally ranged from 20 to 30 nucleotides. For inverse long distance PCR, primer pairs were designed in such a way that the 5' to 3' direction of each primer pointed away from each other.

A pair of inverse long distance PCR primers for cloning DNA98853 were synthesized:
Primer 1 (left primer):
  5' pCATGGTGGGAAGGCCGGTAACG 3' (509-P5) (SEQ ID NO:10)
Primer 2 (right primer):
  5' pGATTGCCAAGAAAATGAGTACTGGGACC 3' (509-P6) (SEQ ID NO:11)

In the inverse long distance PCR reaction, the template is plasmid cDNA library. As a result, the PCR products contain the entire vector sequence in the middle with insert sequences of interest at both ends. After the PCR reaction, the PCR mixture was treated with Dpn I which digests only the template plasmids, followed by agarose gel purification of PCR products of larger than the size of the library cloning vector. Since the primers used in the inverse long distance PCR were also 5'-phosphorylated, the purified products were then self-ligated and transformed into *E.coli* competent cells. Colonies were screened by PCR using 5' vector primer and proper gene specific primer to identify clones with larger 5' sequence. Plasmids prepared from positive clones were sequenced. If necessary, the process could be repeated to obtain more 5' sequences based on new sequence obtained from the previous round.

The purpose of inverse long distance PCR is to obtain the complete sequence of the gene of interest. The clone containing the full length coding region was then obtained by conventional PCR.

The primer pair used to clone the full length coding region of DNA98853 were synthesized:
Forward primer:
  5' ggaggatcgatACCATGGATTGCCAAGAAAATGAG 3' (Cla-MD-509) (SEQ ID NO:12)

Reverse primer:

5' ggaggagcggccgctta AGGGCTGGGAACT-TCAAAGGGCAC (509.TAA.not) (SEQ ID NO:13)

For cloning purposes, a Cla I site and a Not I site were included in the forward primer and reverse primer respectively.

To ensure the accuracy of the PCR products, independent PCR reactions were performed and several cloned products were sequenced.

DNA sequencing of the clones isolated as described above gave the full-length DNA sequence for DNA98853 polypeptide (herein designated as DNA98853-1739) and the derived protein sequence for DNA98853 polypeptide.

The entire nucleotide sequence of DNA98853 is shown in FIG. 1 (SEQ ID NO:1). Clone DNA98853-1739 has been deposited with ATCC and is assigned ATCC Deposit No. ATCC 203906. Clone DNA98853 contains a single open reading frame with an apparent translational initiation site at nucleotide positions 4–6 and ending at the stop codon at nucleotide positions 901–903 (FIG. 1). The predicted polypeptide precursor is 299 amino acids long (FIG. 2). The full-length DNA98853 polypeptide protein shown in FIG. 2 has an estimated molecular weight of about 3.3 kilodaltons and a pI of about 4.72. A potential N-glycosylation site exists between amino acids 74 and 77 of the amino acid sequence shown in FIG. 2. A potential N-myristoylation site exists between amino acids 24 and 29 of the amino acid sequence shown in FIG. 2. Potential casein kinase II phosphorylation sites exist between amino acids 123–126, 185–188, 200–203, 252–255, 257–260, 271–274, and 283–286 of the amino acid sequence shown in FIG. 2. A potential transmembrane domain exists between amino acids 137 to 158 of the sequence shown in FIG. 2. It is presently believed that the polypeptide does not include a signal sequence.

Analysis of the amino acid sequence of the full-length DNA98853 polypeptide suggests that portions of it possess homology to members of the tumor necrosis factor receptor family, thereby indicating that DNA98853 polypeptide may be a novel member of the tumor necrosis factor receptor family. There are three apparent extracellular cysteine-rich domains characteristic of the TNFR family [see, Naismith and Sprang, *Trends Biochem. Sci.*, 23:74–79 (1998)], of which the first two CRDs have 6 cysteines while the third CRD has 4 cysteines.

Example 2

Isolation of cDNA Clones Encoding Human DNA101848 Polypeptide

Based upon the DNA sequence of Incyte clone 509 1511H shown in FIG. 9 (SEQ ID NO:7), oligonucleotides were synthesized to identify by PCR a cDNA library that contained the sequence of interest. These oligonucleotides were:

Forward primer:

5' GAGGGGGCTGGGTGAGATGTG 3' (509–1) (SEQ ID NO:8)

Reverse primer:

5' TGCTTTTGTACCTGCGAGGAGG 3' (509–4AS). (SEQ ID NO:9)

To isolate the full length coding sequence for DNA101848 polypeptide, an inverse long distance PCR procedure was carried out (FIG. 6). The PCR primers generally ranged from 20 to 30 nucleotides. For inverse long distance PCR, primer pairs were designed in such a way that the 5' to 3' direction of each primer pointed away from each other.

A pair of inverse long distance PCR primers for cloning DNA101848 were synthesized:

Primer 1 (left primer):

5' pCATGGTGGGAAGGCCGGTAACG 3' (509-P5) (SEQ ID NO:10)

Primer 2 (right primer):

5' pGATTGCCAAGAAAATGAGTACTGGGACC 3' (509-P6) (SEQ ID NO:11)

In the inverse long distance PCR reaction, the template is plasmid cDNA library. As a result, the PCR products contain the entire vector sequence in the middle with insert sequences of interest at both ends. After the PCR reaction, the PCR mixture was treated with Dpn I which digests only the template plasmids, followed by agarose gel purification of PCR products of larger than the size of the library cloning vector. Since the primers used in the inverse long distance PCR were also 5'-phosphorylated, the purified products were then self-ligated and transformed into *E.coli* competent cells. Colonies were screened by PCR using 5' vector primer and proper gene specific primer to identify clones with larger 5' sequence. Plasmids prepared from positive clones were sequenced. If necessary, the process could be repeated to obtain more 5' sequences based on new sequence obtained from the previous round.

The primer pair used to clone the full length coding region of DNA101848 were synthesized:

Forward primer:

5' ggaggatcgatACCATGGATTGCCAAGAAAATGAG 3' (Cla-MD-509) (SEQ ID NO:12)

Reverse primer:

5' ggaggagcggccgcttaAGGGCTGG-GAACTTCAAAGGGCAC (509.TAA.not) (SEQ ID NO:13)

For cloning purposes, a Cla I site and a Not I site were included in the forward primer and reverse primer respectively.

To ensure the accuracy of the PCR products, independent PCR reactions were performed and several cloned products were sequenced.

DNA sequencing of the clones isolated as described above gave the full-length DNA sequence for DNA101848 polypeptide (herein designated as DNA101848–1739) and the derived protein sequence for DNA101848 polypeptide.

The entire nucleotide sequence of DNA101848 is shown in FIG. 3 (SEQ ID NO:4). Clone DNA101848-1739 has been deposited with ATCC and is assigned ATCC Deposit No. ATCC 203907. Clone DNA101848 contains a single open reading frame with an apparent translational initiation site at nucleotide positions 4–6 and ending at the stop codon at nucleotide positions 895–897 (FIG. 3). The predicted polypeptide precursor is 297 amino acids long (FIG. 4). The full-length DNA101848 polypeptide protein shown in FIG. 4 has an estimated molecular weight of about 3.28 kilodaltons and a pI of about 4.72. A potential N-glycosylation site exists between amino acids 74 and 77 of the amino acid sequence shown in FIG. 4. A potential N-myristoylation site exists between amino acids 24 and 29 of the amino acid sequence shown in FIG. 4. Potential casein kinase II phosphorylation sites exist between amino acids 123–126, 185–188, 200–203, 252–255, 257–260, 271–274, and 283–286 of the amino acid sequence shown in FIG. 4. A potential transmembrane domain exists between amino acids 137 to 158 of the sequence shown in FIG. 4. It is presently believed that the polypeptide does not include a signal sequence.

Analysis of the amino acid sequence of the full-length DNA101848 polypeptide suggests that portions of it possess homology to members of the tumor necrosis factor receptor family, thereby indicating that DNA101848 polypeptide may be a novel member of the tumor necrosis factor receptor family. There are three apparent extracellular cysteine-rich domains characteristic of the TNFR family [see, Naismith and Sprang, *Trends Biochem. Sci.*, 23:74–79 (1998)], of which the first two CRDs have 6 cysteines while the third CRD has 4 cysteines.

To further demonstrate that DNA101848 is indeed a transmembrane protein, two versions of epitope-tagged expression plasmids of DNA101848 were constructed in pRK5B (see Example 11), one with an N-terminal Flag-tag (Flag-DNA101848) and the other with a C-terminal Flag-tag (DNA101848-Flag). MCF-7 cells (ATCC) transfected with either construct (using Lipofectamine reagent; Gibco-BRL) were immunostained with M2 anti-Flag antibody (Sigma) either with or without permeabilization with 0.5% Triton X-100 in PBS. Cell staining was visualized by subsequent incubation with Cy3-conjugated goat anti-mouse (Sigma). As shown FIG. 10, without membrane permeabilization (FIG. 10A and 10B), cell surface staining by M2 antibody was only seen in cells transfected with Flag-DNA101848 but not DNA101848-Flag. When cells were permeabilized before anti-Flag immunostaining, comparable expressions were observed for both types of constructs (FIG. 10C and 10D). This experiment clearly demonstrated that DNA101848 is expressed as a cell surface protein with N-terminal region outside of the cells and C-terminus region inside of the cells. Therefore, DNA101848 represents a type III transmembrane protein.

Example 3

Use of DNA98853 Polyieptide-Encoding DNA or DNA101848 Polypeptide-Encoding DNA as a Hybridization Probe The following method describes use of a nucleotide sequence encoding DNA98853 polypeptide or a nucleotide sequence encoding DNA101848 polypeptide as a hybridization probe.

DNA comprising the coding sequence of full-length DNA98853 polypeptide (as shown in FIG. 1, SEQ ID NO:1) or a fragment thereof is employed as a probe to screen for homologous DNAs (such as those encoding naturally-occurring variants of DNA98853 polypeptide) in human tissue cDNA libraries or human tissue genomic libraries. Similarly, DNA comprising the coding sequence of full-length DNA101848 polypeptide (as shown in FIG. 3, SEQ ID NO:4) or a fragment thereof is employed as a probe to screen for homologous DNAs (such as those encoding naturally-occurring variants of DNA101848 polypeptide) in human tissue cDNA libraries or human tissue genomic libraries.

Hybridization and washing of filters containing either library DNAs is performed under the following high stringency conditions. Hybridization of radiolabeled DNA98853 polypeptide-derived probe or of radiolabeled DNA101848 polypeptide-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SD at 42° C.

DNAs having a desired sequence identity with the DNA encoding full-length native sequence DNA98853 polypeptide or with the DNA encoding full-length native sequence DNA101848 polypeptide can then be identified using standard techniques known in the art.

Example 4

Expression of DNA98853 Polypeptides or DNA101848 Polypeptides in *E. coli*

This example illustrates the preparation of forms of DNA98853 polypeptides and forms of DNA101848 polypeptides by recombinant expression in *E. coli*.

For expression of DNA98853 polypeptide, the DNA sequence encoding the full-length DNA98853 polypeptide (SEQ ID NO:1) or a fragment or variant thereof is initially amplified using selected PCR primers. For expression of DNA101848 polypeptide, the DNA sequence encoding the full-length DNA101848 polypeptide (SEQ ID NO:4) or a fragment or variant thereof is initially amplified using selected PCR primers.

The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the DNA98853 polypeptide coding region or the DNA11848 polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized DNA98853 polypeptide or the solubilized DNA101848 polypeptide can then be purified using a metal chelating column under conditions that allow tight binding of the polypeptide.

Example 5

Expression of DNA98853 Polvpeptides or DNA1O1848 Polvpeptides in Mammalian Cells This example illustrates preparation of forms of DNA98853 polypeptides and DNA101848 polypeptides by recombinant expression in mammalian cells.

The vector, pRK5 (see EP 307,247, published Mar. 15, 1989), is employed as the expression vector. Optionally, the DNA98853 polypeptide-encoding DNA is ligated into pRK5 with selected restriction enzymes to allow insertion of the DNA98853 polypeptide-encoding DNA using ligation methods such as described in Sambrook et al., supra. The resulting vector is called pRK5-DNA98853 polypeptide. Optionally, the DNA101848 polypeptide-encoding DNA is ligated into pRK5 with selected restriction enzymes to allow insertion of the DNA101848 polypeptide-encoding DNA using ligation methods such as described in Sambrook et al., supra. The resulting vector is called pRK5-DNA101848 polypeptide.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-DNA98853 polypeptide DNA is mixed with about 1 microgram DNA encoding the VA RNA gene [Thimmappaya et al., Cell, 31:543 (1982)] and dissolved in 500 μl of 1 mM Tris-HCI, 0.1 mM EDTA, 0.227 M $CaCI_2$. Alternatively, about 10 microgram pRK5-DNA101848 polypeptide DNA is mixed with about 1 μDNA encoding the VA RNA gene [Thimmappaya et al., Cell, 31:543 (1982)] and dissolved in 500 μl of 1 mM Tris-HCI, 0.1 mM EDTA, 0.227 M $CaCI_2$. To the vector mix dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of DNA98853 polypeptide or the presence of DNA101848 polypeptide. The cultures containing transfected cells may undergo further incubation (in serum free medium) and the medium is tested in selected bioassays.

In an alternative technique, DNA98853 polypeptide-encoding DNA or DNA101848 polypeptide-encoding DNA may be introduced into 293 cells transiently using the dextran sulfate method described by Sompayrac et al., Proc. Natl. Acad. Sci., 78:7575 (1981). 293 cells are grown to maximal density in a spinner flask and followed by addition of 700 microgram pRK5-DNA98853 polypeptide DNA, or by addition of 700 jig DNA101848 polypeptide DNA. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed DNA98853 polypeptide or expressed DNA101848 polypeptide can then be concentrated and purified by any selected method, such as dialysis and/or column chromatography.

In another embodiment, DNA98853 polypeptide or DNA101848 polypeptide can be expressed in CHO cells. The pRK5-DNA98853 polypeptide vector or the pRK5-DNA101848 polypeptide vector can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the desired polypeptide, the culture medium may be replaced with serum free medium. Preferably, the cultures are incubated for about 6 days, and then the conditioned medium is harvested. The medium containing the expressed DNA98853 polypeptide or DNA101848 polypeptide can then be concentrated and purified by any selected method.

Epitope-tagged DNA98853 polypeptide or epitope-tagged DNA101848 polypeptide may also be expressed in host CHO cells. The DNA98853 polypeptide-encoding DNA or the DNA101848 polypeptide-encoding DNA may be subcloned out of the pRK5 vector. The subclone insert can undergo PCR to fuse in frame with a selected epitope tag such as a poly-his tag into a Baculovirus expression vector. The poly-his tagged DNA98853 polypeptide-encoding DNA insert or the poly-his tagged DNA101848 polypeptide-encoding DNA insert can then be subcloned into an SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged DNA98853 polypeptide or the expressed poly-His tagged DNA101848 polypeptide can then be concentrated and purified by any selected method, such as by $Ni^{2+}$-chelate affinity chromatography.

Example 6

Expression of a DNA98853 Polypeptide or a DNA101848 Polypeptide in Yeast

The following method describes recombinant expression of DNA98853 polypeptides and DNA101848 polypeptides in yeast.

First, yeast expression vectors are constructed for intracellular production or secretion of DNA98853 polypeptide from the ADH2/GAPDH promoter. DNA encoding the DNA98853 polypeptide of interest, a selected signal peptide and the promoter is inserted into suitable restriction enzyme sites in the selected plasmid to direct intracellular expression of the DNA98853 polypeptide. For secretion, DNA encoding the DNA98853 polypeptide can be cloned into the selected plasmid, together with DNA encoding the ADH2/GAPDH promoter, the yeast alpha-factor secretory signal/leader sequence, and linker sequences (if needed) for expression of the DNA98853 polypeptide.

Alternatively, yeast expression vectors are constructed for intracellular production or secretion of DNA101848 polypeptide from the ADH2/GAPDH promoter. DNA encoding the DNA101848 polypeptide of interest, a selected signal peptide and the promoter is inserted into suitable restriction enzyme sites in the selected plasmid to direct intracellular expression of the DNA101848 polypeptide. For secretion, DNA encoding the DNA101848 polypeptide can be cloned into the selected plasmid, together with DNA encoding the ADH2/GAPDH promoter, the yeast alpha-factor secretory signal/eader sequence, and linker sequences (if needed) for expression of the DNA101848 polypeptide.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant DNA98853 polypeptide or DNA101848 polypeptide can subsequently be isolated and purified by removing the yeast cells from the fermentation medium by centrifugation and then concentrating the medium using selected cartridge filters. The concentrate containing the DNA98853 polypeptide or DNA101848 polypeptide may further be purified using selected column chromatography resins.

Example 7

Expression of DNA98853 Polypeptide or DNA101848 Polypeptides in Baculovirus-Infected Insect Cells The following method describes recombinant expression of DNA98853 polypeptides and DNA101848 polypeptides in Baculovirus-infected insect cells.

The DNA98853 polypeptide-encoding DNA or the DNA101848 polypeptide-encoding DNA is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the DNA98853 polypeptide-encoding DNA or the desired portion of the DNA98853 polypeptide-encoding DNA (such as the sequence encoding the extracellular domain of a transmembrane protein) is amplified by PCR with primers complementary to the 5' and 0 3' regions. Alternatively, the DNA101848 polypeptide-encoding DNA or the desired portion of the DNA101848 polypeptide-encoding DNA (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subdloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4 to 5 days of incubation at 28° C., the released viruses are harvested and used for further amplifications. Viral infection and protein expression is performed as described by O'Reilley et al., Baculovirus expression vectors: A laboratory Manual, Oxford:Oxford University Press (1994).

Expressed poly-his tagged DNA98853 polypeptide or expressed poly-his tagged DNA101848 polypeptide can then be purified, for example, by $Ni^{2+}$-chelate affinity chromatography as follows. Extracts are prepared from recombinant virus-infected Sf9 cells as described by Ruppert et al., *Nature*, 362:175–179 (1993). Briefly, Sf9 cell washed, resuspended in sonication buffer (25 mL Hepes, pH 7.9; 12.5 MM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fun filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $Hisi_0$-tagged DNA98853 polypeptide or the eluted $Hisi_{10}$-tagged DNA101848 polypeptide are pooled and dialyzed against loading buffer.

Alternatively, purification of the IgG tagged (or Fc tagged) DNA98853 polypeptide or the IgG tagged (or Fc tagged) DNA101848 polypeptide can be performed using known chromatography techniques, including for instance, Protein A or protein G column chromatography.

Example 8

Preparation of Antibodies that Bind DNA98853 Polypeptides and/or DNA101848 Polypeptides This example illustrates the preparation of monoclonal antibodies which can specifically bind to DNA98853 polypeptides and/or DNA101848 polypeptides.

Techniques for producing the monoclonal antibodies are known in the art and are described, for instance, in Goding, supra. Immunogens that may be employed include purified DNA98853 polypeptide, purified DNA101848 polypeptide, fusion proteins containing a DNA98853 polypeptide, fusion proteins containing a DNA101848 polypeptide, cells expressing recombinant DNA98853 polypeptide on the cell surface, and cells expressing recombinant DNA101848 polypeptide on the cell surface. Selection of the immunogen can be made by the skilled artisan without undue experimentation.

Mice, such as Balb/c, are immunized with the DNA98853 polypeptide immunogen, or DNA101848 polypeptide immunogen, emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-DNA98853 polypeptide antibodies or DNA101848 polypeptide antibodies.

After a suitable antibody titer has been detected, the animals "positive" for antibodies can be injected with a final intravenous injection of DNA98853 polypeptide or of DNA101848 polypeptide. Three to four days later, the mice are sacrificed and the spleen cells are harvested. The spleen cells are then fused (using 35% polyethylene glycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against DNA98853 polypeptide or for reactivity against DNA101848 polypeptide. Determination of "positive" hybridoma cells secreting the desired monoclonal antibodies against a DNA98853 polypeptide or a DNA101848 polypeptide is within the skill in the art.

The positive hybridoma cells can be injected intraperitoneally into syngeneic Balb/c mice to produce ascites containing the anti-DNA98853 polypeptide monoclonal antibodies or anti-DNA101848 polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

Assays to Detect Expression of DNA101848 Polypeptide mRNA in Human Cells and Tissues Northern Blotting was conducted according to common procedures known to those of skill in the art. Briefly, human polyA+ RNA normal tissue blots or tumor cell line blots (Clontech) were hybridized according to the manufacturer's instructions. $^{32}$P-labeled probes were generated using DNA fragments corresponding to the nucleotides 478–903 of DNA101848 (SEQ ID NO:4). As shown in FIG. 7, relatively high expression levels were detected in two human tumor cell lines, lung carcinoma A549 and melanoma G361. Relatively weak expression levels were also found in prostate, testis, ovary, thyroid, spinal cord and adrenal gland tissues. Interestingly, a smaller transcript with relatively high expression level existed in stomach.

Example 10

Activation of NF-KB

An assay was conducted to determine whether DNA98853 polypeptide or DNA101848 polypeptide induces NF-κB activation by analyzing expression of a reporter gene driven by a promoter containing a NF-$_K$B responsive element from the E-selectin gene.

Human 293 cells (2×10$^5$) (maintained in HG-DMEM supplemented with 10% FBS, 2 mM glutamine, 100 microgram/ml penicillin, and 100 microgram streptomycin) were transiently transfected by calcium phosphate transfection with 0.5 microgram of the firefly luciferase reporter plasmid pGL3.ELAM.tk [Yang et al., Nature, 395:284–288 (1998)] and 0.05 microgram of the Renilla luciferase reporter plasmid (as internal transfection control) (Promega), as well as the indicated additional expression vectors for DNA98853 polypeptide or DNA101848 polypeptide (described above), and carrier plasmid pRKSD to maintain constant DNA between transfections. After 24 hours, the transfected cells were harvested and luciferase activity was assayed as recommended by the manufacturer (Promega). Activities (average of triplicate wells) were normalized for differences in transfection efficiency by dividing firefly luciferase activity by that of Renilla luciferase activity and were expressed as activity relative to that seen in the absence of added expression vectors.

As shown in FIG. 8A, overexpression of flag-tagged DNA101848 polypeptide resulted in significant reporter gene activation. Similar activity was obtained for DNA98853 polypeptide (data not shown).

For the following experiments, only DNA101848 polypeptide was used.

To examine potential intracellular mediators of the DNA101848 polypeptide signaling, dominant negative mutants of certain intracellular signaling molecules involved in the pathways of NF-KB activation by TNF-alpha, IL-1, or LPs-Toll were tested.

The 293 cells were transiently transfected (as above) with the pGL3.ELAM.tk and expression vectors. In addition, the cells were transfected with the following mammalian expression vectors encoding dominant negative forms of TRAF2-DN (aa 87–501); TRAF6-DN (aa 289–522); and NIK-DN [described in Cao et al., Science, 271:1128–1131 (1996); Malinin et al., Nature, 385:540–544 (1997); Muzio et al., Science, 278:1612–1615 (1999) Rothe et al., Science, 269:1424–1427 (1995); Ting et al., EMBO J., 15:6189–6196 (1996); Wesche et al., Immunity, 7:837–847 (1997)]. Luciferase activity was expressed and determined as described above.

The results are shown in FIG. 8B. Co-transfection of a kinase-inactive mutant form of NIK, which acts as a dominant inhibitor of NF-KB activation by TNF-alpha (Malinin et al., Nature, 385:540–544 (1997)), IL-1 (Malinin et al., supra), and LPs-Toll (Yang et al., Nature, 395:284–288 (1998)), substantially blocked NF-KB activation through DNA101848 polypeptide. A dominant negative TRAF2 or dominant negative Traf-6 (Rothe et al., Science, 269:1424–1427 (1995); Rothe et al., Cell: 78:681–692 (1994)) possessing an N-terminal deletion also attenuated NF-KB activation (FIG. 8C). Accordingly, it appears that DNA101848 polypeptide activates NF-KB predominantly through TRAF-2 and TRAF-6.

Example 11

Identification of a Ligand for the DNA101848 Receptor

A chimeric molecule, referred to herein as "AP-EDA-A2", was prepared using human placenta alkaline phosphatase (AP) fused to the N-terminus of an EDA-A2 polypeptide consisting of amino acids 241–389 (Bayes et al., supra). The AP was obtained by PCR amplification using pAPtag-5 (Genehunter Corporation) as a template, and fused and cloned into the expression vector, pCMV-1 Flag (Sigma), with AP at the N-terminus of EDA-A2. The AP-EDA-A2 was transiently transfected (using Lipofectamine reagent; Gibco-BRL) and expressed in human embryonic kidney 293 cells (ATCC). AP-TNF-alpha (Pennica et al., infra) and AP-TALL-1 (amino acids 136–285; sequence disclosed in WO98/18921 published May 7, 1998; Moore et al., Science, 285:260–263 (1999)) were similarly prepared. The conditioned medium from the transfected 293 cells was filtered (0.45 micron), stored at 4° C. in a buffer containing 20mM Hepes (pH 7.0) and 1 mM sodium azide, and used for subsequent cell staining procedures. In addition, a N-terminal Flag-tagged form of EDA-A2 was constructed in a pCMV-I Flag vector. To promote the trimerization of this Flag-tagged EDA-A2 construct, a trimeric form of leucine-zipper sequence [Harbury et al Science. 262:1401–1407 (1993)] was inserted between the Flag-tag and the EDA-A2 (consisting of amino acids 179–389; Bayes et al., supra), and this construct was referred to as Flag-LZP-EDA-A2. Another form of Flag tagged EDA-A2 was also made by cloning amino acids 179–389 of EDA-A2 into pCMV-lFlag vector, and referred to as Flag-EDA-A2. The Flag-LZP-EDA-A2 or Flag-EDA-A2 was purified using M2-agarose gel (Sigma) from serum-free medium of 293 cells transfected with the corresponding expressing plasmid. Flag-TALL-I (consisting of amino acids 136–285; sequence disclosed in WO98/18921 published May 7, 1998; Moore et al., *Science*, 285:260–263 (1999)) was generated in a similar way.

To identify a potential ligand for DNA101848 receptor, COS 7 cells (ATCC) were transiently transfected (using Lipofectainine reagent) with membrane forms of various ligands of TNF family. Among the ligands tested were APRIL, TALL-1, 4–1 BBL, CD27L, CD30L, CD40L, EDA-A2, RANKL, TNF-alpha, and Apo2UIRAIL.

Human TNF-alpha was cloned into pRK5B vector (pRK5B is a precursor of pRK5D that does not contain the SfiI site; see Holmes et al., *Science*, 253:1278–1280 (1991)). For the detection of TNF-alpha expression on the cell surface, a Flag tag was inserted between amino acid 70 and amino acid 71 (using the numbering according to the sequence in Pennica et al., *Nature*, 312:724–729 (1984)). An extracellular region of TALL-1 (aa 75–285; sequ disclosed in WO98/18921 published May 7, 1998; Moore et al., *Science*, 285:260–263 (1999)), 4-IBBL (aa 59–254; Goodwin et al., *Eur. J. Immunol.*, 23:2631–2641 (1993)), CD27 ligand (aa 40–193; Goodwin et al., *Cell*, 73 (1993)), CD30 ligand (aa 61–234; Smith et al., *Cell*, 73:1349–1360 (1993)), RANKL (aa 71–317; see WO98/28426), Apo-2 ligand (aa 40–281; see WO97/25428) or Apo-3L (aa 46–249; see WO99/19490) was individually BamHI site. This resulted in a chimeric ligand with the intracellular and transmembrane regions from TNF-alpha and the extracellular region from the various ligands. For APRIL (Hahne et al., *J. Exp. Med.*, 188:1185–1190 (1998)) and EDA-A2 (Bayes et al., supra), full length cDNA clones without Flag tag were used.

COS 7 (ATCC) cells transfected with various ligands were incubated with DNAIO1848-ECD-hFc or TNFRI-hFc (constructs described below) at 1I g/ml for 1 hour in PBS containing 5% goat serum (Sigma). Cells were subsequently washed three times with PBS and fixed with 4% paraformaldehyde in PBS. Cell staining was visualized by incubation with biotinylated goat anti-human antibody (Jackson Labs, at 1:200 dilution) followed by Cy3-streptavidin (Jackson Labs, at 1:200 dilution). Among all the ligands tested, DNA101848-ECD-hFc only bound EDA-A2 transfected cells. As shown in FIG. I1, DNA101848-hFc but not TNFR-hFc bound to cells transfected with EDA-A2.

To demonstrate the binding of soluble EDA-A2 to cell membrane bound form of DNA101848, COS 7 cells were transfected with 1 microgram DNA101848 (cloned in pRK5B vector) or empty vector plasmid (pRKSB). 18–24 hours after transfection, cells were incubated with conditioned medium containing AP-EDA-A2; AP-TNF-alpha; or AP-TALL-1 for 1 hour at room temperature and stained for AP activity in situ as described in Tartaglia et al., *Cell*, 83:1263–1271 (1995). As shown in FIG. 12, AP-EDA-A2 but not AP-TNF-alpha or AP-TALL-1 specifically bound to cells transfected with DNA101848.

To demonstrate the binding of soluble EDA-A2 to DNA101848 ECD-HFC, one μg of the purified Flag-LZP-EDA-A2 or Flag-EDA-A2 was incubated with 1 μg of purified human immunoadhesin containing the IgGl-Fc fusion of the ECD of DNA101848 (DNA101848-ECD-hFc) or TNFR1-hFC overnight at 4° C in duplicate. The DNA101848-ECD-hFc immunoadhesins were prepared by methods described in Ashkenazi et al., *Proc. Nati. Acad. Sci.*, 88:10535–10539 (1991). The immunoadhesin constructs consisted of amino acids 2–154 of the human DNA 101848 polypeptide (see FIG. 4). The DNA101848-ECD constructs were expressed in CHO cells using a heterologous signal sequence (pre-pro trypsin amino acids 1–17 of pCMV-1 Flag (Sigma)) and encoding the human IgGI Fc region downstream of the DNA101848 sequence, and then purified by protein A affinity chromatography. TNFR1-hFc construct was prepared as described in Ashkenazi et al., *Proc. Natl. Acad, Sci.*, 88:10535–10539 (1991)). Human TNFRSF19-hFc containing amino acids 1–169 (Hu et al., *Genorics*, 62:103–107 (1999prepared as for TNFR1-hFc. The ligand-receptor complex was subjected to immunoprecipitation through the receptor-immunoadhesin with protein A-agarose (Repligen). The immunoprecipitates were then analyzed by Western blot using anti-Flag M2 mAb (Sigma).

The data shows that Flag-LZP-EDA-A2 or Flag-EDA-A2 bound to DNA101848-hFC, but not to TNFR1-hFc or TNFRSF19-hFC (FIG. 13).

Example 12

Interaction between DNA101848 with EDA-A2 Results in Activation of NF-kB 293 cells (ATCC) were seeded 24 hours before transfection at 1×10 cells/well into 12-well plates and transfected with 0.25 μg of ELAM-luciferase reporter gene plasmid, 25 μg pRL-TK (Promega) and the indicated amounts of each expression construct (see FIG. 14). Total amount of transfected DNA was kept constant at 1 μg by supplementation with empty pRKSB vector (see Example 11). In some assay wells, Flag-tagged ligands (prepared as described in Example 11) were added at concentrations indicated 4 hours after transfection. In other assay wells, the cells were co-transfected with full length EDA-A2 (Bayes et al., supra) or TALL-I (sequence disclosed in WO98/18921 published May 7, 1998; Moore et al., *Science*, 285:260–263 (1999)). Cells were harvested 20–24 hours after transfection and reporter gene activity determined with the Dual-Luciferase Reporter Assay System (Promega).

Only minimal activation of NF-kB was observed when DNA101848 was expressed alone at low levels (such as at 0.1 ng). The activation of NF-kB, however, was greatly augmented by either addition of Flag-EDA-A2 or by co-transfection with full length EDA-A2 (FIG. 14).

Treatment of untransfected 293E (Invitrogen) cells with Flag-EDA-A2 (0.2 jglrnl) also resulted in activation of the NF-kB pathway (see FIG. 15A). This was measured by Western Blotting using anti-phospho-IKB-a (New England BioLabs). Preincubation with 20 μg/ml DNA101848-ECD-hFc (see Example 11) abolished IKB-a phosphorylation induced by Flag-EDA-A2 (FIG. 15B). These results suggest that one physiological consequence of DNA101848 and EDA-A2 interaction is activation of the NF-kB pathway.

Deposit of Material

The following materials have been deposited with the American Type Culture Collection, 10801 University Blvd., Manassas, Va. USA (ATCC):

| Material | ATCC Dep. No. | Deposit Date |
|---|---|---|
| DNA98853-1739 | 203906 | April 6, 1999 |
| DNA101848-1739 | 203907 | April 6, 1999 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated DNA98853 polypeptide comprising amino acid residues 1 to 299 of FIG. 2 (SEQ ID NO:3).

2. A chimeric molecule comprising the DNA98853 polypeptide of claim 1 fused to a heterologous amino acid sequence.

3. The chimeric molecule of claim 2, wherein said heterologous amino acid sequence is an epitope tag sequence.

4. The chimeric molecule of claim 2, wherein said heterologous amino acid sequence is a Fc region of an immunoglobulin.

5. A composition comprising an isolated DNA98853 polypeptide of claim 1 and a carrier.

6. The composition of claim 5 wherein said carrier is a pharmaceutically-acceptable carrier.

7. An isolated DNA98853 polypeptide encoded by the cDNA insert of the vector deposited as ATCC Accession No. 203906 (DNA98853).

8. An isolated DNA101848 polypeptide comprising amino acid residues 1 to 297 of FIG. 4 (SEQ ID NO:6).

9. An isolated DNA 101848 polypeptide encoded by the cDNA insert of the vector deposited as ATCC Accession No. 203907 (DNA101848).

10. An isolated DNAIO1848 polypeptide comprising amino acid residues 1 to X of FIG. 4 (SEQ ID NO:6), wherein X is any one of amino acid residues 131–141 of FIG. 4 (SEQ ID NO:6).

11. A composition comprising an isolated DNA101848 polypeptide of claim 8 and a carrier.

12. The composition of claim 11 wherein said carrier is a pharmaceutically-acceptable carrier.

13. A chimeric molecule comprising the DNA101848 polypeptide of claim 8 or claim 10 fused to a heterologous amino acid sequence.

14. The chimeric molecule of claim 13, wherein said heterologous amino acid sequence is an epitope tag sequence.

15. The chimeric molecule of claim 13, wherein said heterologous amino acid sequence is a Fc region of an immunoglobulin.

16. An isolated DNA101848 polypeptide comprising a polypeptide selected from the group consisting of:
  a) a DNA101848 polypeptide comprising amino acid residues 1 to X of FIG. 4 (SEQ ID NO:6), wherein X is any one of amino acid residues 131–141 of FIG. 4 (SEQ ID NO:6); and
  b) a fragment of a), wherein said fragment binds to native sequence EDA-A2 ligand.

17. An isolated DNA98853rpolypeptide consisting of amino acid residues 1 to 299 of FIG. 2 (SEQ ID NO:3).

18. An isolated DNA101848 polypeptide consisting of amino acid residues 1 to 297 of FIG. 4 (SEQ ID NO:6).

19. An isolated polypeptide consisting of amino acid residues 1 to 136 of FIG. 4 (SEQ ID NO:6).

20. An isolated DNA98853 polypeptide having at least 90% amino acid sequence identity to the sequence of amino acid residues 1 to 299 of FIG. 2 (SEQ ID NO:3), wherein said polypeptide activates NF-KB in a mammalian cell or binds to native sequence EDA-A2 ligand.

21. The DNA98853 polypeptide of claim 20, wherein said polypeptide activates NF-KB in a mammalian cell.

22. The DNA98853 polypeptide of claim 20, wherein said polypeptide has at least 95% amino acid sequence identity to the polipeptide of SEQ ID NO: 3.

23. An isolated DNA101848 polypeptide having at least 90% amino acid sequence identity to the sequence of amino acid residues 1 to 297 of FIG. 4 (SEQ ID NO:6), wherein said polypeptide activates NF-KB in a mammalian cell or binds to native sequence EDA-A2 ligand.

24. The DNA101848 polypeptide of claim 23, wherein said polypeptide activates NF-KB in a mammalian cell.

25. The DNA101848 polypeptide of claim 23, wherein said polypeptide has at least 95% amino acid sequence identity to the polypeptide of SEQ ID NO:6.

26. An isolated polypeptide comprising amino acid residues 1 to X of FIG. 4 (SEQ ID NO:6), wherein X is any one of amino acid residues 131–141 of FIG. 4 (SEQ ID NO:6) and said polypeptide binds to native sequence EDA-A2 ligand.

27. The isolated polypeptide of claim 26, wherein said polypeptide activates NF-KB in a mammalian cell.

28. A chimeric molecule comprising the polypeptide of claim 26 fused to a Fc region of an immunoglobulin.

29. A chimeric molecule comprising the polypeptide of claim 26 fused to an epitope tag sequence.

30. An isolated soluble polypeptide comprising a fragment of the extracellular domain sequence of DNA101848 polypeptide that consists of amino acid residues 1 to 136 of FIG. 4 (SEQ ID NO:6), wherein said soluble polypeptide binds to native sequence EDA-A2 ligand.

31. The soluble polypeptide of claim 30 which is fused to a Fc region of an immunoglobulin.

32. The soluble polypeptide of claim 30 which is fused to an epitope tag sequence.

* * * * *